United States Patent
Lind et al.

(10) Patent No.: US 9,797,016 B2
(45) Date of Patent: Oct. 24, 2017

(54) METHODS AND BIOMARKERS FOR DETECTION OF BLADDER CANCER

(75) Inventors: Guro Elisabeth Lind, Oslo (NO); Ragnhild A. Lothe, Oslo (NO); Rolf Inge Skotheim, Oslo (NO); Carmen Jeronimo, Maia (PT); Vera L. Costa, Aulnay-sous-Bois (FR); Rui Henrique, Maia (PT); Manuel R. Teixeira, Vila Nova de Gaia (PT)

(73) Assignee: OSLO UNIVERSITETSSYKEHUS HF, Oslo (NO)

(*) Notice: Subject to any disclaimer, the term of this patent is extended or adjusted under 35 U.S.C. 154(b) by 37 days.

(21) Appl. No.: 13/879,545

(22) PCT Filed: Oct. 19, 2011

(86) PCT No.: PCT/IB2011/002846
§ 371 (c)(1),
(2), (4) Date: Apr. 24, 2013

(87) PCT Pub. No.: WO2012/052844
PCT Pub. Date: Apr. 26, 2012

(65) Prior Publication Data
US 2013/0210011 A1   Aug. 15, 2013

Related U.S. Application Data

(60) Provisional application No. 61/394,478, filed on Oct. 19, 2010.

(51) Int. Cl.
C12Q 1/68   (2006.01)

(52) U.S. Cl.
CPC ...... *C12Q 1/6886* (2013.01); *C12Q 2600/106* (2013.01); *C12Q 2600/112* (2013.01); *C12Q 2600/154* (2013.01)

(58) Field of Classification Search
None
See application file for complete search history.

(56) References Cited

U.S. PATENT DOCUMENTS

| | | | |
|---|---|---|---|
| 2008/0220433 A1* | 9/2008 | Ahlquist et al. | ........... 435/6 |
| 2010/0028872 A1 | 2/2010 | Cairns | |
| 2010/0143899 A1 | 6/2010 | Bosenberg et al. | |
| 2010/0273148 A1 | 10/2010 | Guilford et al. | |

FOREIGN PATENT DOCUMENTS

| | | |
|---|---|---|
| WO | 01/77373 | 10/2001 |
| WO | WO 2008/102002 A2 * | 8/2008 |
| WO | 2010/086388 | 8/2010 |

(Continued)

OTHER PUBLICATIONS

Shirahata, A. et al. Anticancer Research 29:279 (Jan. 2009).*

(Continued)

*Primary Examiner* — Diana B Johannsen
(74) *Attorney, Agent, or Firm* — Casimir Jones, S.C.

(57) ABSTRACT

The invention relates to methods and biomarkers (e.g., epigenetic biomarkers) for detection of bladder cancer in biological samples (e.g., tissue samples, urine samples, urine sediments). In some embodiments, methods and biomarkers of the present invention find use in discriminating between bladder cancer, prostate cancer and renal epithelial tumors.

4 Claims, 8 Drawing Sheets

(56) References Cited

FOREIGN PATENT DOCUMENTS

| WO | 2010/086389 | 8/2010 |
|----|-------------|--------|
| WO | 2010/102823 | 9/2010 |
| WO | 2010/123354 | 10/2010 |

OTHER PUBLICATIONS

Kitamura, Y. et al. Anticancer Research 29:2227 (Jun. 2009).*
Jin, Z. et al. Cancer Research 69:4112 (May 2009).*
Yu, J. et al. Clinical Cancer Research 13(24):7296 (Dec. 2007).*
Costa, Vera L., "Three Epigenetic Biomarkers, GDF15, TMEFF2, and VIM, Accurately Predict Bladder Cancer from DNA-based Analyses of Urine Samples," Clinical Cancer Research, vol. 16, No. 23, Dec. 1, 2010, pp. 5842-5851.
Hellwinkel et al., "Methylation of the TPEF- and PAX6-promoters is increased in early bladder cancer and in normal mucosa adjacent to pTa tumours," BJU Int. Mar. 2008;101(6):753-7. Epub Dec. 7, 2007, pp. 753-757.
International Search Report and Written Opinion dated Mar. 22, 2012, International Patent Application No. PCT/IB2011/002846.
Lokeshwar et al., "Urinary bladder tumor markers," Urologic Oncology, Elsevier, New York, NY, US, vol. 24, No. 6, Nov. 28, 2006, pp. 528-537.

* cited by examiner

A

B

METHODS AND BIOMARKERS FOR DETECTION OF BLADDER CANCER

CROSS-REFERENCE TO RELATED APPLICATIONS

The present invention is a U.S. 371 national phase entry of pending International Patent Application No. PCT/IB2011/002846, international filing date Oct. 19, 2011, which claims priority to U.S. Provisional Patent Application No. 61/394,478, filed Oct. 19, 2010, the contents of which are incorporated by reference in their entireties.

FIELD OF THE INVENTION

The present invention relates to methods and biomarkers (e.g., epigenetic biomarkers) for detection of bladder cancer in biological samples (e.g., tissue samples, urine samples, urine sediment, blood samples, plasma samples, serum samples). In some embodiments, methods and biomarkers of the present invention find use in discriminating between bladder cancer, prostate cancer and renal epithelial tumors.

BACKGROUND OF THE INVENTION

Bladder cancer (BlCa) is one of the leading causes of cancer-related morbidity and mortality. Global estimates for 2002 indicate that approximately 357,000 bladder cancer cases were diagnosed and that approximately 145,000 patients succumbed to the disease (GLOBOCAN 2002: Cancer Incidence, Mortality, and Prevalence Worldwide; IARC Cancerbase No. 4, v. 2.0 ed. Lyon: IARCPress (2004)). In the USA, bladder cancer is the second most common genitourinary (GU) malignancy, with about 71,000 new cases and more than 14,000 deaths in 2009 (Jetnal et al. (2009) CA Cancer J Clin. 59:225-249). The incidence of BlCa increases with age, with an average age at the time of diagnosis in the 60 s, and it is three times more common in men than in women (Kaufman et al. (2009) Lancet 374:239-249). Although several risk factors (e.g., smoking habits and exposure to carcinogens) have been identified, effective strategies for early detection are still not available (Mitra et al. (2009) Ann. Rev. Pathol. 4:251-285).

The present gold standard strategy for BlCa diagnosis is non-invasive voided urine cytology, followed by cystoscopic examination. However, both methods have low sensitivity, especially for low grade tumors (Kaufman et al (2009) Lancet 374:239-249). Several BlCa markers were recently reviewed by Vrooman and Witjes (Vrooman et al. (2008) Eur. Urol. 53:909-916; herein incorporated by reference in its entirety), but were found to be unsuitable for clinical use due to low predictive power and high cost compared with routine urinary cytology. Additional tests have as yet failed to yield diagnostic assays with sufficient sensitivity and specificity for use in clinical settings (Vrooman et al. (2008) Eur. Urol. 53:909-916; Van Tilborg et al. (2009) Int. J. Urol. 16:23-30; each herein incorporated by reference in its entirety).

Urothelial carcinoma comprises the most common form of BlCa, 70% of which present as papillary non-muscle-invasive tumors, although as many as 50-70% of these tumors (pTa and pT1 classified according to AJCC/UICC) (American Joint Committee on Cancer (AJCC) cancer staging manual, 6th ed., Philadelphia, Lippincott-Raven Publisher (2002); herein incorporated by reference in its entirety) will recur and approximately 10-20% will progress to invasive disease (Kaufman et al (2009) Lancet 374:239-249). To predict which patients will progress from superficial to invasive disease remains a challenge. Patients diagnosed with early-stage BlCa undergo frequent monitoring, currently based on cystoscopy and cytology, resulting in BlCa becoming one of the most costly cancer diseases to manage (Bischoff et al. (2009) Curr. Opin. Oncol. 21:272-277; herein incorporated by reference in its entirety). Better, more effective non-invasive tests for early detection of BlCa are needed to lower the morbidity and mortality associated with BlCa.

SUMMARY OF THE INVENTION

The present invention relates to methods and biomarkers (e.g., epigenetic biomarkers) for detection of bladder cancer in biological samples (e.g., tissue samples, urine samples, urine sediment, blood, plasma and serum). In some embodiments, methods and biomarkers of the present invention find use in discriminating between bladder cancer and other cancer types (e.g., prostate cancer, renal epithelial tumors).

In experiments conducted during the course of developing some embodiments of the present invention, epigenetic biomarkers were identified for accurate bladder cancer detection in biological samples (e.g., tissue samples, urine sediments). Gene expression microarray analysis of bladder cancer cell lines treated with 5-aza-2'deoxycytidine and Trichostatin A as well as 26 tissue samples was used to identify biomarkers with altered methylation states in bladder cancer.

Gene methylation levels were quantified in four bladder cancer cell lines, 50 bladder cancer tissues, 20 normal bladder mucosas, and urine sediments from 51 bladder cancer patients and 20 healthy donors, 19 renal cancer patients and 20 prostate cancer patients. ROC curve analysis was used to assess the diagnostic performance of the gene panel. In experiments conducted during the course of developing some embodiments of the present invention, GDF15, HSPA2, TMEFF2, and VIM were identified as epigenetic biomarkers for bladder cancer. The methylation levels of GDF15, HSPA2, TMEFF2, and/or VIM were significantly higher in bladder cancer tissues compared to normal bladder mucosa (P<0.001) and the cancer-specificity was retained in urine sediments (P<0.001). A methylation panel comprising GDF15, TMEFF2 and VIM correctly identified bladder cancer tissues with 100% sensitivity and specificity. In urine samples the panel achieved a sensitivity of 94% and specificity of 100% and an AUC of 0.975. The gene panel and individual members thereof discriminate bladder cancer from both healthy individuals and renal or prostate cancer patients (panel sensitivity: 94%, specificity: 90%).

Accordingly, in some embodiments, the present invention provides methods for predicting a predisposition to cancer (preferably bladder cancer) in a subject, diagnosing a cancer (preferably bladder cancer) in a subject, predicting the likelihood of recurrence of a cancer (preferably bladder cancer) in a subject, providing a prognosis for a subject with cancer (preferably bladder cancer), or selecting a subject with cancer (preferably bladder cancer) for treatment with a particular therapy, comprising: contacting a biological sample from a subject with a reagent for detecting the methylation status of a nucleic acid segment corresponding to the VIM locus; and detecting the methylation status of said nucleic acid segment corresponding to the VIM locus using an in vitro assay, wherein an increased degree of methylation of said nucleic acid segment corresponding to the VIM locus in said sample relative to a reference methylation status provides an indication selected from the group consisting of an indication of a predisposition of the subject to cancer (preferably bladder cancer), an indication that the subject has cancer (preferably bladder cancer), an indication of the likelihood of recurrence of cancer (preferably bladder cancer) in the subject, an indication of survival of the subject, and an indication that the subject is a candidate for treatment with a particular therapy.

In some embodiments, the methods further comprise detecting the methylation status of one more nucleic acid segments corresponding to a locus selected from the group consisting of the GDF15 locus, HSPA2 locus, and TMEFF2 locus, wherein an increased degree of methylation of at least one of said nucleic acid segments corresponding to a locus selected from the group consisting of the GDF15 locus, HSPA2 locus, and TMEFF2 locus in said sample relative to a reference methylation status in addition to said the methylation status of said nucleic acid segment corresponding to the VIM locus provides an indication selected from the group consisting of an indication of a predisposition of the subject to cancer (preferably bladder cancer), an indication that the subject has cancer (preferably bladder cancer), an indication of the likelihood of recurrence of cancer (preferably bladder cancer) in the subject, an indication of survival of the subject, and an indication that the subject is a candidate for treatment with a particular therapy.

In some embodiments, the methods further comprise detecting the methylation status nucleic acid segments corresponding to the GDF15, HSPA2, and TMEFF2 loci, wherein an increased degree of methylation of each of said nucleic acid segments corresponding to a locus selected from the group consisting of the GDF15 locus, HSPA2 locus, and TMEFF2 locus in said sample relative to a reference methylation status in addition to said the methylation status of said nucleic acid segment corresponding to the VIM locus provides an indication selected from the group consisting of an indication of a predisposition of the subject to cancer (preferably bladder cancer), an indication that the subject has cancer (preferably bladder cancer), an indication of the likelihood of recurrence of cancer (preferably bladder cancer) in the subject, an indication of survival of the subject, and an indication that the subject is a candidate for treatment with a particular therapy.

In some embodiments, the methods further comprise generating a risk profile using the results of the contacting and detecting steps. In some embodiments, the bladder cancer is premalignant. In some embodiments, the bladder cancer is malignant. In some embodiments, the biological sample is selected from the group consisting of a tissue sample, a urine sample, and a sample of urine sediment. In some embodiments, the methylation status of the nucleic acid segments is used to discriminate between bladder cancer and another cancer. In some embodiments, the another cancer is selected from the group consisting of prostate cancer and renal epithelial tumors.

In some embodiments, the nucleic acid segment comprises a region selected from the group consisting of a CpG island and a CpG island shore. In some embodiments, the CpG island or shore is present in a coding region or a regulatory region. In some embodiments, the regulatory region is a promoter. In some embodiments, the determining of the level of altered methylation of said nucleic acid segment comprises determining the methylation frequency of said CpG island or island shore. In some embodiments, the determining of the level of a nucleic acid polymer with altered methylation is achieved by a technique selected from the group consisting of methylation-specific PCR, quantitative methylation-specific PCR, methylation-sensitive DNA restriction enzyme analysis, quantitative bisulfite pyrosequencing, and bisulfite genomic sequencing PCR.

In some embodiments, the nucleic acid segments corresponding to a locus selected from the group consisting of the VIM locus, GDF15 locus, HSPA2 locus, and TMEFF2 correspond to all or a portion of the nucleic acid sequences identified by GenBank Accession Numbers NM_003380 (VIM), NM_004864 (GDF15), NM_021979 (HSPA2), or NM_016192 (TMEFF2). In some preferred embodiments, the nucleic acid segments corresponding to a locus selected from the group consisting of the VIM locus, GDF15 locus, HSPA2 locus, and TMEFF2 correspond to the promoter region of the nucleic acid sequences identified by GenBank Accession Numbers NM_003380 (VIM), NM_004864 (GDF15), NM_021979 (HSPA2), or NM_016192 (TMEFF2). In some embodiments, the nucleic acid segments corresponding to a locus selected from the group consisting of the VIM locus, GDF15 locus, HSPA2 locus, and TMEFF2 correspond to the amplicons identified in Table 3. In some embodiments, the nucleic acid segments corresponding to a locus selected from the group consisting of the VIM locus, GDF15 locus, HSPA2 locus, and TMEFF2 correspond to the amplicons bounded (and amplified by) the following primer pairs: SEQ ID NO:1 and 2; SEQ ID NO:3 and 4; SEQ ID NO:5 and 6; SEQ ID NO:7 and 8; SEQ ID NO:9 and 10; SEQ ID NO:11 and 12; SEQ ID NO:13 and 14; SEQ ID NO:15 and 16; SEQ ID NO:17 and 18; SEQ ID NO:19 and 20; SEQ ID NO:21 and 22; SEQ ID NO:23 and 24; SEQ ID NO:25 and 26; SEQ ID NO:28 and 29; SEQ ID NO:31 and 32; SEQ ID NO:34 and 35; SEQ ID NO:37 and 38; and SEQ ID NO:40 and 41. In some embodiments, the nucleic acid segment is a truncated portion of these amplicons, for example, either 10, 20, 30, 40, 50, or 100 bp shorter depending on the length of the amplicon. In other embodiments, the nucleic acid segment is an extended version of the amplicon, for example, extended 10, 20, 30, 40, 50, 100, 200, 300 or more by from either the 5' or 3' end of the amplicon. Identification of the locus corresponding to each amplicon is provided in Table 3 below.

In some embodiments, the reagents for detecting the methylation status of a nucleic acid segment comprise reagents for detecting the methylation status of one or more of the foregoing amplicons, or a truncated or extended version thereof. In some embodiments, the reagents for detecting the methylation status of a nucleic acid segment comprise primer pairs for amplification of one or more of the foregoing amplicons, or a truncated or extended version thereof, and/or one or more probes specific for detection of the amplicon. Examples of suitable probes include, but are not limited to those identified in Table 3 below (e.g., probes encoded by SEQ ID NOs: 27, 30, 33, 36, 39 and/or 42).

In some embodiments, the method permits detection of bladder cancer in said subject with a sensitivity of at least 85% at a specificity of at least 85%. In some embodiments, the method permits detection of bladder cancer in said subject with a sensitivity of at least 80% at a specificity of at least 90%.

In some embodiments, the methods further comprise determining a prognosis for said subject, determining a diagnosis for said subject, or selecting said subject for treatment with a particular therapy.

In some embodiments, the present invention provides a set of methylation specific nucleic acid detection reagents specific for potentially methylated regions of one or more specific loci being suitable to diagnose or predict bladder cancer, wherein said loci comprise one or more of the VIM locus, GDF15 locus, HSPA2 locus, and TMEFF2 locus. In some embodiments, the present invention provides for the use of the set of specific nucleic acid detection reagents for making a diagnostic or prognostic determination of bladder cancer in a subject.

In certain embodiments, the present invention provides a method for detecting bladder neoplasm in a subject comprising: a) obtaining DNA from a biological sample of the subject; b) determining the level, presence, or frequency of methylation of one or more nucleic acid polymers corresponding to a locus such as GDF15, HSPA2, TMEFF2 or VIM. In some embodiments, the nucleic acid comprises a region such as a CpG island or a CpG island shore. In some embodiments, the CpG island or shore is present in a coding region or a regulatory region. In some embodiments, the regulatory region is a promoter. In some embodiments, the determining of the level of altered methylation of a nucleic acid polymer comprises determining the methylation frequency of the CpG island or island shore. In some embodiments, the determining of the level of a nucleic acid polymer with altered methylation is achieved by a technique such as methylation-specific PCR, quantitative methylation-specific PCR, methylation-sensitive DNA restriction enzyme analysis, quantitative bisulfite pyrosequencing, or bisulfite genomic sequencing PCR. In some embodiments, methods of the present invention further comprise: c) generating a risk profile using the results of steps a) and b). In some embodiments, the bladder neoplasm is premalignant. In some embodiments, the bladder neoplasm is malignant. In some embodiments, the method permits detection of bladder cancer in the subject with a sensitivity of at least 85% at a specificity of at least 85%. In some embodiments, the method permits detection of bladder cancer in the subject with a sensitivity of at least 80% at a specificity of at least 90%. In some embodiments, the biological sample is a type such as a tissue sample, a urine sample, a urine sediment sample, a blood sample, a plasma sample or a serum sample.

In certain embodiments, the present invention provides a kit for detecting the presence of a bladder neoplasm in a mammal, the kit comprising reagents useful, sufficient, or necessary for detecting and/or characterizing level, presence, or frequency of methylation of one or more nucleic acid polymers corresponding to a locus such as GDF15, HSPA2, TMEFF2 or VIM.

Additional embodiments will be apparent to persons skilled in the relevant art based on the teachings contained herein.

DEFINITIONS

Figure 1:
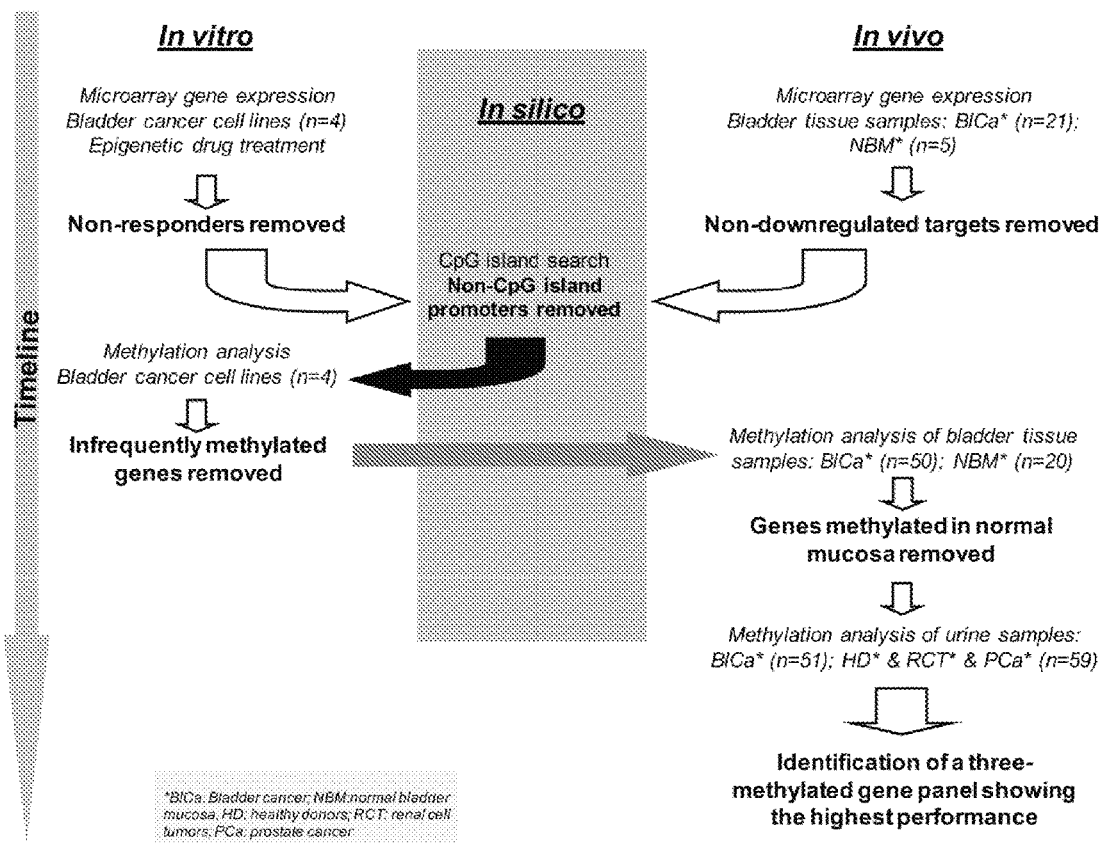
FIG. 1 shows a flow chart depicting steps followed in a study conducted during the course of developing some embodiments of the present invention.

To facilitate an understanding of the present invention, a number of terms and phrases are defined below:

As used herein, the term "sensitivity" is defined as a statistical measure of performance of an assay (e.g., method, test), calculated by dividing the number of true positives by the sum of the true positives and the false negatives.

As used herein, the term "specificity" is defined as a statistical measure of performance of an assay (e.g., method, test), calculated by dividing the number of true negatives by the sum of true negatives and false positives.

As used herein, the term "informative" or "informativeness" refers to a quality of a marker or panel of markers, and specifically to the likelihood of finding a marker (or panel of markers) in a positive sample.

As used herein, the term "CpG island" refers to a genomic DNA region that contains a high percentage of CpG sites relative to the average genomic CpG incidence (per same species, per same individual, or per subpopulation (e.g., strain, ethnic subpopulation, or the like). Various parameters and definitions for CpG islands exist; for example, in some embodiments, CpG islands are defined as having a GC percentage that is greater than 50% and with an observed/expected CpG ratio that is greater than 60% (Gardiner-Garden et al. (1987) J Mol. Biol. 196:261-282; Baylin et al. (2006) Nat. Rev. Cancer 6:107-116; Irizarry et al. (2009) Nat. Genetics 41:178-186; each herein incorporated by reference in its entirety). In some embodiments, CpG islands may have a GC content>55% and observed CpG/expected CpG of 0.65 (Takai et al. (2007) PNAS 99:3740-3745; herein incorporated by reference in its entirety). Various parameters also exist regarding the length of CpG islands. As used herein, CpG islands may be less than 100 bp; 100-200 bp, 200-300 bp, 300-500 bp, 500-750 bp; 750-1000 bp; 100 or more bp in length. In some embodiments, CpG islands show altered methylation patterns relative to controls (e.g., altered methylation in cancer subjects relative to subjects without cancer; tissue-specific altered methylation patterns; altered methylation in biological samples (e.g., urine, urine sediment, tissue, blood, plasma, serum) from subjects with bladder neoplasia (e.g., bladder cancer) relative to subjects without bladder neoplasia). In some embodiments, altered methylation involves hypermethylation. In some embodiments, altered methylation involves hypomethylation.

As used herein, the term "CpG shore" or "CpG island shore" refers to a genomic region external to a CpG island that is or that has potential to have altered methylation patterns (see, e.g., Irizarry et al. (2009) Nat. Genetics 41:178-186; herein incorporated by reference in its entirety). CpG island shores may show altered methylation patterns relative to controls (e.g., altered methylation in cancer subjects relative to subjects without cancer; tissue-specific altered methylation patterns; altered methylation in biological samples (e.g., urine, urine sediment, tissue) from subjects with bladder neoplasia (e.g., bladder cancer) relative to subjects without bladder neoplasia). In some embodiments, altered methylation involves hypermethylation. In some embodiments, altered methylation involves hypomethylation. CpG island shores may be located in various regions relative to CpG islands (see, e.g., Irizarry et al. (2009) Nat. Genetics 41; 178-186; herein incorporated by reference in its entirety). Accordingly, in some embodiments, CpG island shores are located less than 100 bp; 100-250 bp; 250-500 bp; 500-1000 bp; 1000-1500 bp; 1500-2000 bp; 2000-3000 bp; 3000 bp or more away from a CpG island.

As used herein, the term "metastasis" is meant to refer to the process in which cancer cells originating in one organ or part of the body relocate to another part of the body and continue to replicate. Metastasized cells subsequently form tumors which may further metastasize. Metastasis thus refers to the spread of cancer from the part of the body where it originally occurs to other parts of the body. As used herein, the term "metastasized bladder cancer cells" is meant to refer to bladder cancer cells which have metastasized; bladder cancer cells localized in a part of the body other than the bladder.

As used herein, "an individual is suspected of being susceptible to metastasized bladder cancer" is meant to refer to an individual who is at an above-average risk of developing metastasized bladder cancer. Examples of individuals at a particular risk of developing bladder cancer are those whose family medical history indicates above average incidence of bladder cancer among family members and/or those who have already developed bladder cancer and have been effectively treated who therefore face a risk of relapse and recurrence. Other factors which may contribute to an above-average risk of developing metastasized bladder cancer which would thereby lead to the classification of an individual as being suspected of being susceptible to metastasized bladder cancer may be based upon an individual's specific genetic, medical and/or behavioral background and characteristics.

The term "neoplasm" as used herein refers to any new and abnormal growth of tissue. Thus, a neoplasm can be a premalignant neoplasm or a malignant neoplasm. The term "neoplasm-specific marker" refers to any biological material that can be used to indicate the presence of a neoplasm. Examples of biological materials include, without limitation, nucleic acids, polypeptides, carbohydrates, fatty acids, cellular components (e.g., cell membranes and mitochondria), and whole cells. The term "bladder neoplasm-specific marker" refers to any biological material that can be used to indicate the presence of a bladder neoplasm (e.g., a premalignant bladder neoplasm; a malignant bladder neoplasm). Examples of bladder neoplasm-specific markers include, but are not limited to, GDF15, TMEFF2, HSPA2, and VIM.

As used herein, the term "amplicon" refers to a nucleic acid generated using primer pairs. The amplicon is typically single-stranded DNA (e.g., the result of asymmetric amplification), however, it may be RNA or dsDNA.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR; see, e.g., U.S. Pat. No. 5,494,810; herein incorporated by reference in its entirety) are forms of amplification. Additional types of amplification include, but are not limited to, allele-specific PCR (see, e.g., U.S. Pat. No. 5,639,611; herein incorporated by reference in its entirety), assembly PCR (see, e.g., U.S. Pat. No. 5,965,408; herein incorporated by reference in its entirety), helicase-dependent amplification (see, e.g., U.S. Pat. No. 7,662,594; herein incorporated by reference in its entirety), hot-start PCR (see, e.g., U.S. Pat. Nos. 5,773,258 and 5,338,671; each herein incorporated by reference in their entireties), intersequence-specfic PCR, inverse PCR (see, e.g., Triglia, et al. (1988) Nucleic Acids Res., 16:8186; herein incorporated by reference in its entirety), ligation-mediated PCR (see, e.g., Guilfoyle, R. et al., Nucleic Acids Research, 25:1854-1858 (1997); U.S. Pat. No. 5,508,169; each of which are herein incorporated by reference in their entireties), methylation-specific PCR (see, e.g., Herman, et al., (1996) PNAS 93(13) 9821-9826; herein incorporated by reference in its entirety), miniprimer PCR, multiplex ligation-dependent probe amplification (see, e.g., Schouten, et al., (2002) Nucleic Acids Research 30(12): e57; herein incorporated by reference in its entirety), multiplex PCR (see, e.g., Chamberlain, et al., (1988) Nucleic Acids Research 16(23) 11141-11156; Ballabio, et al., (1990) Human Genetics 84(6) 571-573; Hayden, et al., (2008) BMC Genetics 9:80; each of which are herein incorporated by reference in their entireties), nested PCR, overlap-extension PCR (see, e.g., Higuchi, et al., (1988) Nucleic Acids Research 16(15) 7351-7367; herein incorporated by reference in its entirety), real time PCR (see, e.g., Higuchi, et al., (1992) Biotechnology 10:413-417; Higuchi, et al., (1993) Biotechnology 11:1026-1030; each of which are herein incorporated by reference in their entireties), reverse transcription PCR (see, e.g., Bustin, S. A. (2000) J. Molecular Endocrinology 25:169-193; herein incorporated by reference in its entirety), solid phase PCR, thermal asymmetric interlaced PCR, and Touchdown PCR (see, e.g., Don, et al., Nucleic Acids Research (1991) 19(14) 4008; Roux, K. (1994) Biotechniques 16(5) 812-814; Hecker, et al., (1996) Biotechniques 20(3) 478-485; each of which are herein incorporated by reference in their entireties). Polynucleotide amplification also can be accomplished using digital PCR (see, e.g., Kalinina, et al., Nucleic Acids Research. 25; 1999-2004, (1997); Vogelstein and Kinzler, Proc Natl Acad Sci USA. 96; 9236-41, (1999); International Patent Publication No. WO05023091A2; US Patent Application Publication No. 20070202525; each of which are incorporated herein by reference in their entireties).

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like) and at a suitable temperature and pH). The primer is typically single stranded for maximum efficiency in amplification, but may alternatively be double stranded. If double stranded, the primer is generally first treated to separate its strands before being used to prepare extension products. In some embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method. In certain embodiments, the primer is a capture primer.

As used herein, the term "nucleic acid molecule" refers to any nucleic acid containing molecule, including but not limited to, DNA or RNA. The term encompasses sequences that include any of the known base analogs of DNA and RNA including, but not limited to, 4 acetylcytosine, 8-hydroxy-N-6-methyladenosine, aziridinylcytosine, pseudoisocytosine, 5-(carboxyhydroxyl-methyl)uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP).

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., $H^+$, $NH_4^+$, $Na^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) Meth Enzymol. 68: 90-99; the phosphodiester method of Brown et al. (1979) Meth Enzymol. 68: 109-151; the diethylphosphoramidite method of Beaucage et al. (1981) Tetrahedron Lett. 22: 1859-1862; the triester method of Matteucci et al. (1981) J Am Chem Soc. 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

A "sequence" of a biopolymer refers to the order and identity of monomer units (e.g., nucleotides, etc.) in the biopolymer. The sequence (e.g., base sequence) of a nucleic acid is typically read in the 5' to 3' direction.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

The term "gene" refers to a nucleic acid (e.g., DNA) sequence that comprises coding sequences necessary for the production of a polypeptide, RNA (e.g., including but not limited to, mRNA, tRNA and rRNA) or precursor. The polypeptide, RNA, or precursor can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences". Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) processed transcript. The mRNA functions during translation to specify the sequence or order of amino acids in a nascent polypeptide.

The term "locus" as used herein refers to a nucleic acid sequence on a chromosome or on a linkage map and includes the coding sequence as well as 5' and 3' sequences involved in regulation of the gene.

DETAILED DESCRIPTION OF THE INVENTION

The present invention relates to methods and biomarkers (e.g., epigenetic biomarkers) for detection of bladder cancer in biological samples (e.g., tissue samples, urine samples, urine sediment, blood, plasma, serum). In some embodiments, methods and biomarkers of the present invention find use in discriminating between bladder cancer, prostate cancer and renal epithelial tumors.

Bladder cancer is a heterogeneous group of tumors that follow diverse pathways of development and progression. Because tumor behavior is difficult to predict, novel diagnostic and prognostic markers for BlCa, especially non-muscle invasive tumors, is required to provide risk-adjusted treatment and surveillance. Although urine cytology is very sensitive for high-grade tumor detection, low-grade tumors are difficult to identify and diagnostic performance relies heavily on the operator's proficiency (Kaufman et al. (2009) Lancet 374:239-249; herein incorporated by reference in its entirety). Desirable qualities of a diagnostic test include high sensitivity and specificity, limited interobserver variability, cost-effectiveness and ease of performance.

Epigenetic alterations, and DNA methylation in particular, are cancer hallmarks (Cairns (2007) Nat. Rev. Cancer 7:531-543; herein incorporated by reference in its entirety). In experiments conducted during the development of some embodiments of the present invention, novel epi-markers were identified for sensitive and specific detection of BlCa in voided urine samples, enabling their use for early detection and patient monitoring as an alternative strategy to cystoscopy and urine cytology. In some embodiments, a three-gene panel (GDF15, TMEFF2, and VIM) selected based on stringent criteria, was able to accurately identify BlCa both in tissue an urine samples with sensitivity and specificity of 94% and 100%, respectively. The performance of this gene panel clearly exceeded that of conventional cytopathology, as it correctly identified BlCa in 30 out of 31 (97%) cases, whereas cytology only clearly diagnosed as malignant 10 out of the 31 (32%) of cases. Moreover, the panel was able to discriminate urine samples of BlCa positive patients from patients with other urological tumors. Previous reports on the feasibility of detecting BlCa through methylation profiling of tumor tissues were qualitative rather than quantitative and were hampered by lack of ability to differentially detect BlCa from other types of urological tumors (Catto et al. (2005) J. Clin. Oncol. 23:2903-2910; Friedrich et al. (2005) Eur. J. Cancer 41:2769-2778; Kim et al. (2008) J. Urol. 180:1141-1145; Jarmalaite et al. (2008) Oncology 75:145-151; Brait et al. (2008) Cancer Epidemiol. Biomarkers Prev. 17:2786-2794; Friedrich et al. (20040 Clin. Cancer Res. 10:7457-7465; Dulaimi et al. (2004) Clin Cancer Res. 10:1887-1893; Hoque et al. (2006) J. Matl. Cancer Inst. 98:996-1004; Yu et al. (2007) Clin Cancer Res. 13:7296-7304; Ellinger et al. (2008) J. Urol. 179:346-352; Negraes et al. (2008) BMC Cancer 8:238; each herein incorporated by reference in its entirety). The same approach has been also attempted in urine samples from BlCa patients, but with essentially the same caveats and lower sensitivity (Friedrich et al. (2004) Clin. Cancer Res. 10:7457-7465; Dulaimi et al. (2004) Clin Cancer Res. 10:1887-1893; Hoque et al. (2006) J. Matl. Cancer Inst. 98:996-1004; Yu et al. (2007) Clin Cancer Res. 13:7296-7304; Ellinger et al. (2008) J. Urol. 179:346-352; Negraes et al. (2008) BMC Cancer 8:238; each herein incorporated by reference in its entirety). Although marker specificity has been higher in most of those studies, the performance of the gene panels was not tested against other urological tumors and thus it is likely that specificity and positive predictive value would decrease. In some embodiments, marker panels described herein have the ability to discriminate BlCa from prostate and renal cancer retaining both high specificity and sensitivity. In some embodiments, individual markers or panels may be used in combination with additional genes specific for prostate and/or renal cancers.

To generate the gene panel tested during the course of developing some embodiments of the present invention, microarray gene expression profiling was used in combination with 5-aza-dC and TSA treatment of bladder cancer cell lines to identify epigenetically inactivated gene targets. Prior studies using high-throughput strategies to uncover epigenetically de-regulated genes in BlCa have failed to yield makers with clinically useful levels of specificity and sensitivity. Using CpG microarrays, Aleman and co-workers (Aleman et al. (2008) Br. J. Cancer 98:466-473; herein incorporated by reference in its entirety) associated SOX9 promoter methylation with bladder cancer progression, but the methylation frequency of 56.4% is much lower than for some marker panels described herein. Both FGF18 and MMP11 were found to be down-regulated in response to 5-aza-2'-cytidine and zebularine treatment and have been proposed as potential epi-markers for BlCa, but they were not tested in tumor tissues nor in urine samples (Veerla et al. (2008) Genes Chromosomes Cancer 47:368-378; herein incorporated by reference in its entirety). Renard et al. (Renard et al. (2009) Eur. Urol. 58:96-104; herein incorporated by reference in its entirety) were able to detect BlCa in urine samples with 90% sensitivity and 93% specificity with a two-gene panel (TWIST1 and NID2), which was superior to cytology. Although the sensitivity of our three-gene panel was slightly lower, specificity was 100% in urine samples. Moreover, cases of prostate or renal cell cancer were not included as controls in the aforementioned studies, preventing differential detection. The added value of this approach is clearly illustrated by a case in our series which was initially allocated in the renal cell carcinoma set of urines. Because the gene panel tested positive in this case, the clinical files were re-analyzed showing that this renal cell cancer patient was diagnosed with BlCa three years after the collection of the urine sample. Although this is an anecdotal case, it suggests that epigenetic alterations do, indeed, precede clinical manifestations of disease and are thereby represent promising biomarkers for early cancer detection.

Interestingly, the candidate target gene list found in experiments described herein is different from those that used similar methodological approaches (Aleman et al. (2008) 98:466-473; Veerla et al. (2008) Genes Chromosomes Cancer 47:368-378; Renard et al. Eur. Urol. 58:96-104; each herein incorporated by reference in its entirety). Several strict criteria were included to limit the probability of selecting false positives (Lind et al. (2006) Cell Oncol. 28:25-272; herein incorporated by reference in its entirety).

Only array elements up-regulated more than 4-fold in at least two of the four cell lines analyzed were chosen. Then, the expression level of these genes was subsequently examined in primary bladder carcinomas and normal bladder mucosa, and only genes found to be down-regulated were further selected.

The putative biological relevance of GDF15, HSPA2, TMEFF2 and VIM gene promoter methylation in carcinogenesis may provide additional support to the methodology described herein. Both TMEFF2 (located at chromosome band 2q32.3, encoding a transmembrane protein with EGF-like and two follistatin-like domains 2, involved in cell proliferation control) and VIM (located at chromosome band 10p13, encoding the intermediate filament vimentin) have been previously found to be silenced through aberrant promoter methylation in esophageal, gastric and colon cancer (Young et al. (2001) PNAS USA 98:265-270; Chen et al. (2005) J. Natl. Cancer Inst. 97:1124-1132; Zou et al. (20070 Cancer Epidemiol. Biomarkers Prev. 16:2686-2696; Shirahata et al. (2009) Anticancer Res. 29:279-281; Tsunoda et al. (2009) Oncol. Rep. 21:1067-1073; Jin et al. (2009) Cancer Res. 69:4112-4115; Kitamura et al. (2009) Anticancer Res. 29:2227-2229; each herein incorporated by reference in its entirety). Interestingly, a higher frequency of TMEFF2 promoter methylation in tumor tissue compared to morphologically normal tumor-adjacent tissue has been reported for bladder cancer (Hellwinkel et al. (2008) BJU Int. 101:753-757; herein incorporated by reference in its entirety), although no association with grade or stage was apparent. Nevertheless, the presence of TMEFF2 promoter methylation in apparently normal bladder mucosa shows that this epigenetic alteration arises early in bladder carcinogenesis and supports its use as an epi-marker for early cancer detection. The VIM promoter methylation has been proposed as colorectal tumor marker (Chen et al. (2005) J. Natl. Cancer Inst. 97:1124-1132; Zou et al. (20070 Cancer Epidemiol. Biomarkers Prev. 16:2686-2696; Shirahata et al. (2009) Anticancer Res. 29:279-281; each herein incorporated by reference in its entirety) and is currently included in a non-invasive test for colorectal cancer (ColoSure™). VIM methylation is a "true" early diagnostic marker in colorectal cancer without biological function as it is not expressed as a protein in the mucosa epithelium of the large bowel (Chen et al. (2005) J. Natl. Cancer Inst. 97:1124-1132; herein incorporated by reference in its entirety). Data described herein show for the first time the value of the VIM marker for bladder cancer prediction in urine samples.

This is the first report of an association between GDF15 (located at chromosome band 19p13.11) and HSPA2 (located at chromosome band 14q24.1) promoter methylation and bladder cancer. GDF15 encodes a divergent member of the transforming growth factor-B superfamily, a large family of secreted molecules required for normal development, differentiation, and tissue homeostasis. Its anti-tumorigenic activity has been suggested due to the association between GDF15 over-expression and tumor growth arrest and increased apoptosis (Baek et al. (2001) Mol. Pharmacol. 59:901-908; herein incorporated by reference in its entirety). However, other reports suggest a pro-tumorigenic role, as high expression of GDF15 is frequently observed in several tumors (Nakamura et al. (2003) Br. J. Cancer 88:1101-1104; Eling et al. (2006) J. Biochem. Mol. Biol. 39:649-655; each herein incorporated by reference in its entirety). Thus, while the present invention is not limited to any particular mechanism, and an understanding of the mechanism is not necessary to practice the present invention, it is contemplated that like other members of the TGF-β superfamily, GFD15 might act as a tumor suppressor in early cancer stages and as a pro-tumorigenic at later stages of tumor progression (Eling et al. (2006) J. Biochem. Mol. Biol. 39:649-655; herein incorporated by reference in its entirety). Interestingly, data reported herein fit well with this hypothesis as GDF15 promoter methylation was cancer specific but a decrease in methylation levels was apparent from low to high grade tumors and from superficial to muscle-invasive tumors. Interestingly, the GDF15 gene promoter has been previously reported to be more densely methylated in renal cancer cell lines (including two derived from primary tumors) than in normal kidney cells, although no information is provided concerning primary renal tumors (Ibanez de Caceres et al. (2006) 66:5021-5028; herein incorporated by reference in its entirety). Indeed, GDF15 promoter methylation occurred in urine sediments from renal cancer patients, but it was mostly vestigial and only 1 out of 19 cases was above the cutoff value. Thus, although BlCa and RCT might share GDF15 promoter methylation, a quantitative assay is able to accurately discriminate those cancers.

Therefore, using a highly sensitive automated and quantitative screening methodology for detecting cancer-related promoter methylation, novel epi-biomarkers and epi-biomarker panels were identified that are frequently and specifically methylated in bladder cancer. Moreover, in come embodiments, a three-gene panel derived from that set was able to discriminate between tumorous and non-tumorous bladder tissue with high sensitivity and specificity. Finally, in some embodiments, this panel finds use for early and accurate detection of bladder cancer in urine samples, even when patients with kidney or prostate cancer were used as controls.

While the present invention exemplifies several markers specific for detecting bladder cancer, any marker that is correlated with the presence or absence of bladder cancer may be used. A marker, as used herein, includes, for example, nucleic acid(s) whose production or mutation or lack of production is characteristic of a bladder neoplasm. Depending on the particular set of markers employed in a given analysis, the statistical analysis will vary. For example, where a particular combination of markers is highly specific for bladder cancer, the statistical significance of a positive result will be high. It may be, however, that such specificity is achieved at the cost of sensitivity (e.g., a negative result may occur even in the presence of bladder cancer). By the same token, a different combination may be very sensitive (e.g., few false negatives, but has a lower specificity).

Particular combinations of markers may be used that show optimal function with different ethnic groups or sex, different geographic distributions, different stages of disease, different degrees of specificity or different degrees of sensitivity. Particular combinations may also be developed which are particularly sensitive to the effect of therapeutic regimens on disease progression. Subjects may be monitored after a therapy and/or course of action to determine the effectiveness of that specific therapy and/or course of action.

The methods of the present invention are not limited to particular indicators of bladder neoplasm.

In some embodiments, indicators of bladder neoplasm include, for example, epigenic alterations. Epigenetic alterations include but are not limited to DNA methylation (e.g., CpG methylation). In some embodiments, the level (e.g., frequency, score) of methylation (e.g., hypermethylation relative to a control, hypomethylation relative to a control) is determined without limitation to the technique used for such determining. Methods of the present invention are not limited to particular epigenetic alterations (e.g., DNA methylation) (e.g., CpG methylation) (e.g., CpG methylation in coding or regulatory regions GDF15, HSPA2, TMEFF2 and VIM). Altered methylation may occur in, for example, CpG islands; CpG island shores; or regions other than CpG islands or CpG island shores.

In certain embodiments, methods, kits, and systems of the present invention involve determination of methylation state of a locus of interest (e.g., in human DNA) (e.g., in human DNA extracted from a urine sample, from a bladder tissue sample, from a tumor sample, from a blood sample, from a serum sample, from a plasma sample etc). Any appropriate method can be used to determine whether a particular DNA is hypermethylated or hypomethylated. Standard PCR techniques, for example, can be used to determine which residues are methylated, since unmethylated cytosines converted to uracil are replaced by thymidine residues during PCR. PCR reactions can contain, for example, 10 µL, of captured DNA that either has or has not been treated with sodium bisulfite, 1×PCR buffer, 0.2 mM dNTPs, 0.5 µM sequence specific primers (e.g., primers flanking a CpG island or CpG shore within the captured DNA), and 5 units DNA polymerase (e.g., Amplitaq DNA polymerase from PE Applied Biosystems, Norwalk, Conn.) in a total volume of 50 µl. A typical PCR protocol can include, for example, an initial denaturation step at 94° C. for 5 min, 40 amplification cycles consisting of 1 minute at 94° C., 1 minute at 60° C., and 1 minute at 72° C., and a final extension step at 72° C. for 5 minutes.

To analyze which residues within a captured DNA are methylated, the sequences of PCR products corresponding to samples treated with and without sodium bisulfite can be compared. The sequence from the untreated DNA will reveal the positions of all cytosine residues within the PCR product. Cytosines that were unmethylated will be converted to thymidine residues in the sequence of the bisulfite-treated DNA, while residues that were methylated will be unaffected by bisulfite treatment.

Similarly, in some embodiments, methods of the present invention involve the determination (e.g., assessment, ascertaining, quantitation) of methylation level of an indicator of bladder neoplasm (e.g., the mutation level of a CpG island or CpG shore in the coding or regulatory region of a gene locus) in a sample (e.g., a DNA sample extracted from urine). A skilled artisan understands that an increased, decreased, informative, or otherwise distinguishably different methylation level is articulated with respect to a reference (e.g., a reference level, a control level, a threshold level, or the like). For example, the term "elevated methylation" as used herein with respect to the methylation status (e.g., CpG DNA methylation) of a gene locus (e.g., GDF15, HSPA2, TMEFF2 and VIM) is any methylation level that is above a median methylation level in a urine sample from a random population of mammals (e.g., a random population of 10, 20, 30, 40, 50, 100, or 500 mammals) that do not have a bladder neoplasm (e.g., bladder cancer). Elevated levels of methylation can be any level provided that the level is greater than a corresponding reference level. For example, an elevated methylation level of a locus of interest (e.g., GDF15, HSPA2, TMEFF2 and VIM) methylation can be 0.5, 1, 2, 3, 4, 5, 6, 7, 8, 9, 10, or more fold greater than the reference level methylation observed in a normal urine sample. It is noted that a reference level can be any amount. The term "elevated methylation score" as used herein with respect to detected methylation events in a matrix panel of particular nucleic acid markers is any methylation score that is above a median methylation score in a urine sample from a random population of mammals (e.g., a random population of 10, 20, 30, 40, 50, 100, or 500 mammals) that do not have a bladder neoplasm (e.g., bladder cancer). An elevated methylation score in a matrix panel of particular nucleic acid markers can be any score provided that the score is greater than a corresponding reference score. For example, an elevated score of methylation in a locus of interest (e.g., GDF15, HSPA2, TMEFF2 and VIM) can be 0.5, 1, 2, 3, 4, 5, 6, 7, 8, 9, 10, or more fold greater than the reference methylation score observed in a normal urine sample. It is noted that a reference score can be any amount.

The methods are not limited to a particular type of mammal. In some embodiments, the mammal is a human. In some embodiments, the bladder neoplasm is premalignant. In some embodiments, the bladder neoplasm is malignant. In some embodiments, the bladder neoplasm is bladder cancer without regard to stage of the cancer (e.g., stage I, II, III, or IV).

The present invention also provides methods and materials to assist medical or research professionals in determining whether or not a mammal has a bladder neoplasm (e.g., bladder cancer). Medical professionals can be, for example, doctors, nurses, medical laboratory technologists, and pharmacists. Research professionals can be, for example, principle investigators, research technicians, postdoctoral trainees, and graduate students. A professional can be assisted by (1) determining the ratio of particular markers in a urine sample, and (2) communicating information about the ratio to that professional, for example.

After the level (score, frequency) of particular markers in a urine, blood, serum or plasma sample is reported, a medical professional can take one or more actions that can affect patient care. For example, a medical professional can record the results in a patient's medical record. In some cases, a medical professional can record a diagnosis of a bladder neoplasia, or otherwise transform the patient's medical record, to reflect the patient's medical condition. In some cases, a medical professional can review and evaluate a patient's entire medical record, and assess multiple treatment strategies, for clinical intervention of a patient's condition. In some cases, a medical professional can record a prediction of tumor occurrence with the reported indicators. In some cases, a medical professional can review and evaluate a patient's entire medical record and assess multiple treatment strategies, for clinical intervention of a patient's condition.

A medical professional can initiate or modify treatment of a bladder neoplasm after receiving information regarding the level (score, frequency) associated with markers in a patient's urine, blood, serum or plasma sample. In some cases, a medical professional can compare previous reports and the recently communicated level (score, frequency) of markers, and recommend a change in therapy. In some cases, a medical professional can enroll a patient in a clinical trial for novel therapeutic intervention of bladder neoplasm. In some cases, a medical professional can elect waiting to begin therapy until the patient's symptoms require clinical intervention.

A medical professional can communicate the assay results to a patient or a patient's family. In some cases, a medical professional can provide a patient and/or a patient's family with information regarding bladder neoplasia, including treatment options, prognosis, and referrals to specialists, e.g., oncologists and/or radiologists. In some cases, a medical professional can provide a copy of a patient's medical records to communicate assay results to a specialist. A research professional can apply information regarding a subject's assay results to advance bladder neoplasm research. For example, a researcher can compile data on the assay results, with information regarding the efficacy of a drug for treatment of bladder neoplasia to identify an effective treatment. In some cases, a research professional can obtain assay results to evaluate a subject's enrollment, or continued participation in a research study or clinical trial. In some cases, a research professional can classify the severity of a subject's condition, based on assay results. In some cases, a research professional can communicate a subject's assay results to a medical professional. In some cases, a research professional can refer a subject to a medical professional for clinical assessment of bladder neoplasia, and treatment thereof. Any appropriate method can be used to communicate information to another person (e.g., a professional). For example, information can be given directly or indirectly to a professional. For example, a laboratory technician can input the assay results into a computer-based record. In some cases, information is communicated by making a physical alteration to medical or research records. For example, a medical professional can make a permanent notation or flag a medical record for communicating a diagnosis to other medical professionals reviewing the record. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

It is noted that a single urine sample can be analyzed for one bladder neoplasm-specific marker or for multiple bladder neoplasm-specific markers. In preferred embodiments, a single urine sample is analyzed for multiple bladder neoplasm-specific markers, for example, using multi-marker assays. In addition, multiple urine samples can be collected for a single mammal and analyzed as described herein. In some embodiments, a urine sample is split into first and second portions, where the first portion undergoes cytological analysis and the second portion undergoes further purification or processing (e.g., sequence-specific capture step(s) (e.g., for isolation of specific markers for analysis of methylation levels). In some embodiments, the urine sample undergoes one or more preprocessing steps before being split into portions. In some embodiments, the urine sample is treated, handled, or preserved in a manner that promotes DNA integrity and/or inhibits DNA degradation (e.g., through use of storage buffers with stabilizing agents (e.g., chelating agents, DNase inhibitors) or handling or processing techniques that promote DNA integrity (e.g., immediate processing or storage at low temperature (e.g., −80 degrees C.)).

In some embodiments, all the basic essential materials and reagents required for detecting bladder neoplasia through detecting both the level (presence, absence, score, frequency) of markers in a urine sample obtained from the mammal are assembled together in a kit. Such kits generally comprise, for example, reagents useful, sufficient, or necessary for detecting and/or characterizing one or more markers specific for a bladder neoplasm (e.g., methylation status of GDF15, HSPA2, TMEFF2 and VIM). In some embodiments, the kits contain enzymes suitable for amplifying nucleic acids including various polymerases, deoxynucleotides and buffers to provide the necessary reaction mixture for amplification. In some embodiments, the kits of the present invention include a means for containing the reagents in close confinement for commercial sale such as, e.g., injection or blow-molded plastic containers into which the desired reagent are retained. Other containers suitable for conducting certain steps of the disclosed methods also may be provided.

In some embodiments, the methods disclosed herein are useful in monitoring the treatment of bladder neoplasia (e.g., bladder cancer). For example, in some embodiments, the methods may be performed immediately before, during and/or after a treatment to monitor treatment success. In some embodiments, the methods are performed at intervals on disease free patients to ensure treatment success.

The present invention also provides a variety of computer-related embodiments. Specifically, in some embodiments the invention provides computer programming for analyzing and comparing a pattern of bladder neoplasm-specific marker detection results in a urine sample obtained from a subject to, for example, a library of such marker patterns known to be indicative of the presence or absence of a bladder neoplasm, or a particular stage or bladder neoplasm.

In some embodiments, the present invention provides computer programming for analyzing and comparing a first and a second pattern of bladder neoplasm-specific marker detection results from a urine sample taken at least two different time points. In some embodiments, the first pattern may be indicative of a pre-cancerous condition and/or low risk condition for bladder cancer and/or progression from a pre-cancerous condition to a cancerous condition. In such embodiments, the comparing provides for monitoring of the progression of the condition from the first time point to the second time point.

In yet another embodiment, the invention provides computer programming for analyzing and comparing a pattern of bladder neoplasm-specific marker detection results from a urine sample to a library of bladder neoplasm-specific marker patterns known to be indicative of the presence or absence of a bladder cancer, wherein the comparing provides, for example, a differential diagnosis between a benign bladder neoplasm, and an aggressively malignant bladder neoplasm (e.g., the marker pattern provides for staging and/or grading of the cancerous condition).

The methods and systems described herein can be implemented in numerous ways. In one embodiment, the methods involve use of a communications infrastructure, for example the internet. Several embodiments of the invention are discussed below. It is also to be understood that the present invention may be implemented in various forms of hardware, software, firmware, processors, distributed servers (e.g., as used in cloud computing) or a combination thereof. The methods and systems described herein can be implemented as a combination of hardware and software. The software can be implemented as an application program tangibly embodied on a program storage device, or different portions of the software implemented in the user's computing environment (e.g., as an applet) and on the reviewer's computing environment, where the reviewer may be located at a remote site (e.g., at a service provider's facility).

For example, during or after data input by the user, portions of the data processing can be performed in the user-side computing environment. For example, the user-side computing environment can be programmed to provide for defined test codes to denote platform, carrier/diagnostic test, or both; processing of data using defined flags, and/or generation of flag configurations, where the responses are transmitted as processed or partially processed responses to the reviewer's computing environment in the form of test code and flag configurations for subsequent execution of one or more algorithms to provide a results and/or generate a report in the reviewer's computing environment.

The application program for executing the algorithms described herein may be uploaded to, and executed by, a machine comprising any suitable architecture. In general, the machine involves a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the application program (or a combination thereof) which is executed via the operating system. In addition, various other peripheral devices may be connected to the computer platform such as an additional data storage device and a printing device.

As a computer system, the system generally includes a processor unit. The processor unit operates to receive information, which generally includes test data (e.g., specific gene products assayed), and test result data (e.g., the pattern of bladder neoplasm-specific marker detection results from a urine sample). This information received can be stored at least temporarily in a database, and data analyzed in comparison to a library of marker patterns known to be indicative of the presence or absence of a pre-cancerous condition, or known to be indicative of a stage and/or grade of bladder cancer.

Part or all of the input and output data can also be sent electronically; certain output data (e.g., reports) can be sent electronically or telephonically (e.g., by facsimile, e.g., using devices such as fax back). Exemplary output receiving devices can include a display element, a printer, a facsimile device and the like. Electronic forms of transmission and/or display can include email, interactive television, and the like. In some embodiments, all or a portion of the input data and/or all or a portion of the output data (e.g., usually at least the library of the pattern of bladder neoplasm-specific marker detection results known to be indicative of the presence or absence of a pre-cancerous condition) are maintained on a server for access, e.g., confidential access. The results may be accessed or sent to professionals as desired.

A system for use in the methods described herein generally includes at least one computer processor (e.g., where the method is carried out in its entirety at a single site) or at least two networked computer processors (e.g., where detected marker data for a urine sample obtained from a subject is to be input by a user (e.g., a technician or someone performing the assays)) and transmitted to a remote site to a second computer processor for analysis (e.g., where the pattern of bladder neoplasm-specific marker) detection results is compared to a library of patterns known to be indicative of the presence or absence of a pre-cancerous condition), where the first and second computer processors are connected by a network, e.g., via an intranet or internet). The system can also include a user component(s) for input; and a reviewer component(s) for review of data, and generation of reports, including detection of a pre-cancerous condition, staging and/or grading of a bladder neoplasm, or monitoring the progression of a pre-cancerous condition or a bladder neoplasm. Additional components of the system can include a server component(s); and a database(s) for storing data (e.g., as in a database of report elements, e.g., a library of marker patterns known to be indicative of the presence or absence of a pre-cancerous condition and/or known to be indicative of a grade and/or a stage of a bladder neoplasm, or a relational database (RDB) which can include data input by the user and data output. The computer processors can be processors that are typically found in personal desktop computers (e.g., IBM, Dell, Macintosh), portable computers, mainframes, minicomputers, or other computing devices.

The input components can be complete, stand-alone personal computers offering a full range of power and features to run applications. The user component usually operates under any desired operating system and includes a communication element (e.g., a modem or other hardware for connecting to a network), one or more input devices (e.g., a keyboard, mouse, keypad, or other device used to transfer information or commands), a storage element (e.g., a hard drive or other computer-readable, computer-writable storage medium), and a display element (e.g., a monitor, television, LCD, LED, or other display device that conveys information to the user). The user enters input commands into the computer processor through an input device. Generally, the user interface is a graphical user interface (GUI) written for web browser applications.

The server component(s) can be a personal computer, a minicomputer, or a mainframe, or distributed across multiple servers (e.g., as in cloud computing applications) and offers data management, information sharing between clients, network administration and security. The application and any databases used can be on the same or different servers. Other computing arrangements for the user and server(s), including processing on a single machine such as a mainframe, a collection of machines, or other suitable configuration are contemplated. In general, the user and server machines work together to accomplish the processing of the present invention.

Where used, the database(s) is usually connected to the database server component and can be any device which will hold data. For example, the database can be any magnetic or optical storing device for a computer (e.g., CDROM, internal hard drive, tape drive). The database can be located remote to the server component (with access via a network, modem, etc.) or locally to the server component.

Where used in the system and methods, the database can be a relational database that is organized and accessed according to relationships between data items. The relational database is generally composed of a plurality of tables (entities). The rows of a table represent records (collections of information about separate items) and the columns represent fields (particular attributes of a record). In its simplest conception, the relational database is a collection of data entries that "relate" to each other through at least one common field.

Additional workstations equipped with computers and printers may be used at point of service to enter data and, in some embodiments, generate appropriate reports, if desired. The computer(s) can have a shortcut (e.g., on the desktop) to launch the application to facilitate initiation of data entry, transmission, analysis, report receipt, etc. as desired.

In certain embodiments, the present invention provides methods for obtaining a subject's risk profile for developing bladder neoplasm (e.g., bladder cancer). In some embodiments, such methods involve obtaining a urine or blood sample from a subject (e.g., a human at risk for developing bladder cancer; a human undergoing a routine physical examination), detecting the presence, absence, or level (e.g., methylation frequency or score) of one or more markers specific for a bladder neoplasm in or associated with the urine, blood, plasma or serum sample (e.g., specific for a bladder neoplasm) in the urine, blood, plasma or serum sample, and generating a risk profile for developing bladder neoplasm (e.g., bladder cancer) based upon the detected level (score, frequency) or presence or absence of the indicators of bladder neoplasia. For example, in some embodiments, a generated risk profile will change depending upon specific markers and detected as present or absent or at defined threshold levels. The present invention is not limited to a particular manner of generating the risk profile. In some embodiments, a processor (e.g., computer) is used to generate such a risk profile. In some embodiments, the processor uses an algorithm (e.g., software) specific for interpreting the presence and absence of specific exfoliated epithelial markers as determined with the methods of the present invention. In some embodiments, the presence and absence of specific markers as determined with the methods of the present invention are imputed into such an algorithm, and the risk profile is reported based upon a comparison of such input with established norms (e.g., established norm for pre-cancerous condition, established norm for various risk levels for developing bladder cancer, established norm for subjects diagnosed with various stages of bladder cancer). In some embodiments, the risk profile indicates a subject's risk for developing bladder cancer or a subject's risk for re-developing bladder cancer. In some embodiments, the risk profile indicates a subject to be, for example, a very low, a low, a moderate, a high, and a very high chance of developing or re-developing bladder cancer. In some embodiments, a health care provider (e.g., an oncologist) will use such a risk profile in determining a course of treatment or intervention (e.g., biopsy, wait and see, referral to an oncologist, referral to a surgeon, etc.).

The following examples are provided in order to demonstrate and further illustrate certain preferred embodiments and aspects of the present invention and are not to be construed as limiting the scope thereof.

Example 1

Prediction of Bladder Cancer from DNA Isolated from Urine Samples Using GDF15, TMEFF2, and/or VIM as Epigenetic Biomarkers Materials and Methods A flow chart depicting the different steps followed in this study is provided in FIG. 1.

Cancer Cell Lines

Cell lines representative of bladder (5637, J82, SCaBER, and TCCSUP), renal cell (786-0, ACHN, Caki-1, Caki-2) and prostate (22Rv1, DU 145, LNCaP, PC-3) cancer were obtained from the American Type Culture Collection (Manassas, Va.). All cell lines were cultured according to the manufacturer's specifications, with 10% fetal bovine serum (Gibco, Invitrogen, Carlsbad, Calif.) and antibiotics (100 units/mL penicillin G, and 100 µg/mL streptomycin, Gibco), in a humidified atmosphere of 5% $CO_2$ at 37° C.

All BlCa cell lines were subjected to treatment with a combination of the demethylating drug 5-aza-2'deoxycytidine (1 µM for 72 h) and the histone deacetylase inhibitor trichostatin A (0.5 µM added the last 12 h). In parallel, the same cell lines were cultured without treatment for 72 hours and were harvested before confluency.

Patients and Tumor Sample Collection

The 50 BlCa samples included in experiments described herein were obtained from a consecutive series of patients diagnosed and treated between a 12-month span. Tumor tissues were collected after transurethral resection or radical cystectomy. A small tumor sample was immediately snap-frozen, stored at −80° C., and subsequently cut in cryostat for DNA and RNA extraction. The bulk material was routinely processed for routine pathological examination allowing for tumor classification and WHO/ISUP grading (Epstein et al. (1998) Am. J. Surg. Pathol. 22:1435-1448; NCCN Clinical Practice Guidelines in Oncology, Bladder Cancer, National Comprehensive Cancer Network (2009); each herein incorporated by reference in its entirety). An independent set of 20 normal bladder mucosas from BlCa-free individuals (prostate cancer patients submitted to radical prostatectomy) was used as controls. Relevant clinical data was collected from patient's clinical records (see Table 1).

TABLE 1

Clinical and histopathological parameters of patients with bladder tumors and normal bladder mucosa.

| Clinicopathological features | BlCa | NBM |
|---|---|---|
| Patients, n | 50 | 20 |
| Gender, n (%) | | |
| Male | 41 (82) | 20 (100) |
| Female | 9 (18) | 0 (0) |
| Median age, yrs (range) | 71 (33-92) | 63 (49-75) |
| Pathological stage, n (%) | | |
| pTa | 17 (34) | n.a. |
| pT1 | 21 (42) | n.a. |
| pT2 | 11 (22) | n.a. |
| pT3 | 0 (0) | n.a. |
| pT4 | 1 (2) | n.a. |
| Grade, n (%) | | |
| Papillary, low-grade | 19 (38) | n.a. |
| Papillary, high-grade | 24 (48) | n.a. |
| Invasive, high-grade | 7 (14) | n.a. |

BlCa, bladder cancer;
NBM, normal bladder mucosa;
n.a, not applicable

Urine Sample Collection and Processing

Morning voided urine samples (one per patient) were collected from 51 patients with BlCa diagnosed and treated over a two-year span, from 19 patients with renal cell tumor and from 20 patients with prostate cancer. Controls were randomly chosen among healthy donors with no personal or family history of cancer. Relevant demographic data is provided in Table 2. Patients and controls were enrolled after informed consent. Urine storage and processing conditions were standardised: each sample was immediately centrifuged at 4000 rpm for 10 minutes; the pelleted urine sediment was then washed twice with phosphate-buffered saline, and stored at −80° C.

TABLE 2

Gender and age distribution of healthy donors (HD), and bladder cancer (BlCa), renal cell tumor (RCT) and prostate cancer (PCa) patients which provided urine samples for this study.

| | HD | BlCa | RCT | PCa | HD & RCT & PCa |
|---|---|---|---|---|---|
| Patients, n | 20 | 51 | 19 | 20 | 59 |
| Gender, n (%) | | | | | |
| Male | 3 (15) | 40 (78) | 5 (26) | 20 (100) | 28 (47) |
| Female | 17 (85) | 11 (22) | 14 (74) | 0 (0) | 31 (53) |
| Median age, yrs (range) | 47 (39-65) | 72 (42-93) | 63 (33-87) | 65 (53-88) | 59 (33-88) |

Isolation of Nucleic Acids

DNA was extracted from the frozen urine cell pellets and treated and untreated cancer cell lines using a standard phenol-chloroform procedure. Total RNA from cancer cell lines was isolated using Trizol (Invitrogen, Carlsbad, Calif.). From tissue samples, DNA and total RNA were extracted using the AllPrep DNA/RNA Mini Kit (Qiagen Inc., Valencia, Calif.). DNA and RNA concentrations were determined using a ND-1000 Nanodrop (NanoDrop Technologies, Wilmington, USA), and the RNA quality was measured in a 2100 Bioanalyzer (Agilent Technologies, Palo Alto, Calif.).

Gene Expression Microarrays

Treated and untreated BlCa cell lines were analyzed with the Applied Biosystems Human Genome Survey Microarray (P/N 4337467, Foster City, Calif.), which contains 31,700 60-mer oligonucleotide probes representing 27,868 individual human genes. Digoxigenin-UTP labeled cRNA was generated and amplified from 1.5 µg of total RNA from each sample using Applied Biosystems Chemiluminescent RT-IVT Labeling Kit (P/N 4365716) according to the manufacturer's protocol. Array hybridization was performed for 16 hrs at 55° C. using 10 µg of the labeled cRNA. Chemiluminescence detection, image acquisition and analysis were performed using an Applied Biosystems Chemiluminescence Detection Kit (P/N 4342142) and Applied Biosystems 1700 Chemiluminescent Microarray Analyzer (P/N 4338036) following the manufacturer's protocol. Images were auto-gridded and the chemiluminescent signals were quantified, background subtracted, and spot- and spatially-normalized using the above mentioned Microarray Analyzer software. All samples were post-processed and normalized with the R-script "ABarray" and Bioconductor. Normalized post-processed data had a selected cut off of 25% relatively to the array signal.

Microarray analysis of bladder carcinomas (n=21) and normal bladder mucosa samples (n=5) was performed in parallel. The relative gene expression in tumor samples was calculated using the median value of expression of the normal tissues.

Arrays elements up-regulated more than four-fold after 5-aza-2'-deoxycytidine and trichostatin A treatment in at least two of four bladder cancer cell lines, and simultaneously downregulated in tumor samples compared with normal tissue were considered to be targets for DNA methylation.

CpG Island Search, Bisulfite Treatment and Methylation-Specific Polymerase Chain Reaction (MSP)

The resulting top 100 target genes from the microarray approach were analysed for the presence of promoter CpG islands. The RefSeqs were retrieved from the UCSC Genome browser database, including 1000-bp upstream and 500-bp downstream of the transcription start point. Presence of promoter CpG islands was determined using default settings in the CpG Island Searcher software (Takai et al. (2002) PNAS USA 99:3740-3745; herein incorporated by reference in its entirety). For CpG island-containing genes, MSP primers specific to methylated and unmethylated sequences were designed using the Methyl Primer Express Software v1.0 (Applied Biosystems). Primer sequences are summarized in Table 3 (Weisenberger et al. (2005) Nucleic Acids Res. 33:6823-6836; herein incorporated by reference in its entirety), along with amplicon lengths, positions, and PCR conditions. Prior to MSP analyses DNA samples were bisulfite modified. Tissue samples were treated with the EpiTect bisulfite kit (Qiagen Inc., Valencia, Calif.), and bladder and urine samples were treated with the EZ DNA methylation—Gold kit (Zymo Research, Orange, Calif.). The modified DNA was eluted in 60 µL of water, and then stored at −80° C.

TABLE 3

Sequences of the primers and probes used in the conventional and quantitative methylation-specific PCR experiments, and bisulfite sequencing, with sizes and amplicons generated.

| Primer set | GenBank accession n° | Sense primer sequence (5'-3') | Antisense primer sequence (5'-3') | Probe Sequence | Product size, bp | Annealing temp., ° C. |
|---|---|---|---|---|---|---|
| GDF15_MSP_U | NM_004864 | ATT TGG TGG TTA TTT GTA TTT GT (SEQ ID NO: 1) | AAC AAT CAT ATC ACA TCC CAC A (SEQ ID NO: 2) | n.a. | 135 | 57 |
| GDF15_MSP_M | | CGG CGG TTA TTT GTA TTT GC (SEQ ID NO: 3) | AAC GAT CGT ATC ACG TCC C (SEQ ID NO: 4) | n.a. | 132 | 60 |
| HSPA2_MSP_U | NM_021979 | TTA TAA GAA TTG GGA ATT GGG T (SEQ ID NO: 5) | AAA TCA ATA CCA ATA ACC AAA (SEQ ID NO: 6) | n.a. | 176 | 55 |
| HSPA2_MSP_M | | TAA GAA TCG GGA ATT GGG C (SEQ ID NO: 7) | AAT CGA TAC CGA TAA CCG AA (SEQ ID NO: 8) | n.a. | 172 | 58 |
| TMEFF2_MSP_U | NM_016192 | GGA AGA GGG GTG TTA GTT (SEQ ID NO: 9) | AAC ACT AAC CCA AAT AAA ACT (SEQ ID NO: 10) | n.a. | 153 | 55 |
| TMEFF2_MSP_M | | GAA GAG GGG CGT TAG TTC (SEQ ID NO: 11) | ACG CTA ACC CGA ATA AAA CT (SEQ ID NO: 12) | n.a. | 151 | 57 |
| VIM_MSP_U | NM_003380 | GGG TTA TAA AAA TAG TGT TTT TGG T (SEQ ID NO: 13) | ACA ATA ACA CAA ACT AAC TCC CA (SEQ ID NO: 14) | n.a. | 149 | 56 |
| VIM_MSP_M | | TTATAAAAATAGCGTTTTCGGC (SEQ ID NO: 15) | ATAACGCGAACTAACTCCCG (SEQ ID NO: 16) | n.a. | 143 | 59 |
| GDF15_BSP | | TGT GGG TGA TTA GTT TTT TTA T (SEQ ID NO: 17) | ACC CAA CCC AAA TCT TCC (SEQ ID NO: 18) | n.a. | 436 | 59 |

TABLE 3-continued

Sequences of the primers and probes used in the conventional and quantitative methylation-specific PCR experiments, and bisulfite sequencing, with sizes and amplicons generated.

| Primer set | GenBank accession n° | Sense primer sequence (5'-3') | Antisense primer sequence (5'-3') | Probe Sequence | Product size, bp | Annealing temp., °C |
|---|---|---|---|---|---|---|
| HSPA2_BSP | | GTA AGT TTG TGG TGG AGT TG (SEQ ID NO: 19) | AAT CTC CAC CTT ACC ATA TTA AA (SEQ ID NO: 20) | n.a. | 306 | 56 |
| TMEFF2_BSP | | TTA TTT TTA GTT YGG AGA GAC (SEQ ID NO: 21) | GAA AAC CAC AAA TAA ACT CR (SEQ ID NO: 22) | n.a. | 244 | 57 |
| VIM_BSP | | GGT TGG GAT GGT AGT G (SEQ ID NO: 23) | GTA ACT CCR ACT AAA ACT C (SEQ ID NO: 24) | n.a. | 310 | 58 |
| ACTB_QMSP | Y00474 | TGG TGA TGG AGG AGG TTT AGT AAG T (SEQ ID NO: 25) | AAC CAA TAA AAC CTA CTC CTC CCT TAA (SEQ ID NO: 26) | FAM 5' ACC ACC ACC CAA CAC ACA ATA ACA AAC ACA 3' TAMRA (SEQ NO: 27) | 133 | 60 |
| ALUC4_QMSP | [14] | GGT TAG GTA TAG TGG TTT ATA TTT GTA ATT TTA GTA (SEQ ID NO: 28) | ATT AAC TAA ACT AAT CTT AAA CTC CTA ACC TCA (SEQ ID NO: 29) | FAM 5' CCT ACC TTA ACC TCC C-MGB 3' (SEQ NO: 30) | 98 | 60 |
| GDF15_QMSP | | TCG GCG GTT ATT TGT ATT TGC (SEQ ID NO: 31) | CGT CGA AAA CAA CCG AAA CA (SEQ ID NO: 32) | 5' FAM-TTT TCG AGG TTT TTC G-MGB 3' (SEQ NO: 33) | 101 | 60 |
| HSPA2_QMSP | | TTT CGT TTT AAC GTC GTT CGT TT (SEQ ID NO: 34) | CCG ACG CAC GAA TAA ATA ATA CC (SEQ ID NO: 35) | 5' FAM-TCG GTT ATC GGT ATC GAT-MGB 3' (SEQ NO: 36) | 92 | 60 |
| TMEFF2_QMSP | | GTT CGG GGT TAC GCG C (SEQ ID NO: 37) | TTC GCC TCA CTC TCC GCT (SEQ ID NO: 38) | 5' FAM-TCG GAT TTC GTT TTC GGT AG-MGB 3' (SEQ NO: 39) | 83 | 60 |
| VIM_QMSP | | TTC GGG AGT TAG TTC GCG TT (SEQ ID NO: 40) | ACC GCC GAA CAT CCT ACG A (SEQ ID NO: 41) | 5' FAM-TCG TCG TTT AGG TTA TCG T-MGB 3' (SEQ NO: 42) | 108 | 60 |

The promoter methylation status of the first 20-25 CpG island containing target genes was analyzed in BlCa cell lines. Genes methylated in all four BlCa cell lines were also analyzed in renal and prostate cancer cell lines in order to determine their tumor-specificity. All results were confirmed with a second independent round of MSP. Bisulfite treated DNA from normal lymphocytes and in vitro methylated human DNA (Chemicon International, Temecula, Calif.) represented the unmethylated and the methylated positive control, respectively. Water, replacing bisulfite treated template, was the negative control in both reactions. PCR amplifications were performed as follows: a 10-minute 94° C. incubation step followed by 35 cycles of 94° C. for 30 seconds, annealing temperature for 30 seconds, and 72° C. for 30 seconds. A 7-minute elongation step at 72° C. completed the PCR amplification program. PCR products were loaded onto nondenaturing 2% agarose gels, stained with ethidium bromide and visualized under an ultraviolet transilluminator.

Real-Time Quantitative Methylation-Specific Polymerase Chain Reaction (qMSP)

Primers and probes for real-time quantitative methylation-specific polymerase chain reaction (qMSP), were specifically designed to bind to bisulfite converted DNA (Eads et al. (2000) Nucleic Acids Res. 28:E32; herein incorporated by reference in its entirety), spanning 11 to 13 CpG dinucleotides. Sequences and annealing temperatures are provided in Table 3. GDF15, HSPA2, TMEFF2 and VIM were amplified and normalized for DNA input using ALU as a reference gene. Amplification reactions were carried out in triplicates consisting of 10 μL of TaqMan Universal PCR Master Mix No AmpErase UNG (Applied Biosystems); 900 nM concentration of forward and reverse primers; 200 nM of probe; and 3 μL of bisulfite modified DNA as a template, and were carried out at 95° C. for 10 minutes, followed by 45 cycles at 95° C. for 15 seconds and 60° C. for 1 minute, in 384-well plates in a 7900HT Fast Real-Time PCR System (Applied Biosystems), and analyzed by a sequence detector system (SDS 2.3, Applied Biosystems). Each plate included patient DNA samples, positive (in vitro methylated human DNA, Chemicon) and negative (normal leukocyte human DNA) controls, and multiple water blanks Leukocyte DNA from a healthy individual was methylated in vitro with excess SssI methyltransferase (New England Biolabs) to generate completely methylated DNA, and serial dilutions (32.5-0.052 ng) of this DNA were used to construct a calibration curve for each plate to quantify the amount of fully methylated alleles in each reaction.

A run was considered valid when the following six criteria were met: (1) slopes of each standard curve above −3.60 corresponding to a PCR efficiency>90%; (2) $R^2$ of at least four relevant data points≥0.99; (3) no template controls not amplified; (4) the positive methylation control had to provide a methylated signal; (5) the negative control had no signal; and (6) threshold cycle value for each gene≤40.

The relative level of methylated DNA for each gene in each sample was determined using the following formula: $[(gene/ALU)^{sample}/(gene/ALU)^{in\ vitro\ methylated\ DNA}] \times 1000$. To categorize samples as methylated or unmethylated, a cutoff value was chosen based on the highest methylation ratio value of the respective normal samples, ensuring the specificity of the assay.

Bisulfite Sequencing

GDF15, HSPA2, TMEFF2 and VIM were subjected to direct bisulfite sequencing in BlCa cell lines. Primer sequences, overlapping with the MS-PCR products, amplicons, and annealing temperatures are listed in Table 3. PCR reactions included a 10-minute 94° C. denaturation step followed by 40 cycles of 94° C. for 30 seconds, annealing temperature for 30 seconds, and 72° C. for 30 seconds. PCR products were loaded onto a nondenaturing 2% agarose gels, stained with ethidium bromide and visualized under an ultraviolet transilluminator. Excess primer and nucleotides were removed by Illustra GFX PCR DNA and Gel Band Purification kit (GE Healthcare, USB Corporation, Cleveland, Ohio) following the protocol of the manufacturer. The purified products were sequenced using the dGTP BigDye Terminator Cycle Sequencing Ready Reaction kit (Applied Biosystems) in an ABI PRISM™ 310 Genetic Analyzer (Applied Biosystems). The approximate amount of methyl cytosine of each CpG site was calculated by comparing the peak height of the cytosine signal with the sum of the cytosine and thymine peak height signals (Melki et al. (1999) Cancer Res. 59:3730-3740; herein incorporated by reference in its entirety). CpG sites with ratios 0-0.20, 0.21-0.80, and 0.81-1.0 were considered unmethylated, partially methylated, and fully methylated, respectively.

Quantitative Gene Expression Analyses

RNA from four bladder cancer cell lines untreated, treated either with 1 µM or 5 µM of 5-aza-2'-deoxycytidine for 72 hours, and treated with the combination of 1 µM of 5-aza-dC (72 h) and 0.5 µM of trichostatin (added the last 12 h) was analyzed. For each sample, 0.5 µg of total RNA was reverse transcribed into cDNA using the RevertAid™ H Minus First Strand cDNA Synthesis Kit (Fermentas Inc., Glen Burnie, Md.), including random hexamer primers. cDNA was used as template for real-time PCR reaction. GDF15 (Hs00171132_m1), HSPA2 (Hs00356607_g1), TMEFF2 (Hs01086901_m1), VIM (Hs00185584_m1), and endogenous controls assays GUSB (Hs99999908_m1) and HPRTJ (Hs99999909_m1), were amplified separately in 96-well plates following the recommended protocol (Applied Biosystems), and the real time quantitative gene expression was measured by the 7500 Real-Time PCR System (Applied Biosystems). All samples were analyzed in triplicate, and the mean value was used for data analysis. The human universal reference RNA (Stratagene, La Jolla, Calif.) was used to generate a standard curve on each plate, and the resulting quantitative expression levels of the tested genes were normalized against the mean value of the two endogenous controls to obtain a ratio that was then multiplied by 1000 for easier tabulation.

Statistics

Differences in quantitative methylation values were assessed by the Kruskall-Wallis test, followed by pairwise comparisons using the Mann-Whitney U-test. The relationship between methylation ratios and other standard clinicopathological variables (gender, tumor stage, grade), were evaluated using the Mann-Whitney or Kruskall-Wallis tests. A Spearman nonparametric correlation test was additionally performed to compare age and methylation levels. Disease-specific survival curves (Kaplan-Meier with log rank test) were computed for standard variables such as tumor stage and grade, and also for methylation status. A receiver operator characteristics (ROC) curve was created by plotting the true positive rate (sensitivity) against the false-positive rate (1-specificity), and the area under the curve (AUC) was calculated. All two-tailed P-values were derived from statistical tests using a computer-assisted program (SPSS version 15.0, Chicago, Ill.), and considered statistically significant at P<0.05.

Identification of a List of Novel DNA Methylation Candidate Targets in Bladder Cancer Five hundred and eighty microarray elements were found to be up-regulated at least four-fold after the epigenetic-modulating treatment in at least two out of four BlCa cell lines analyzed. Among these elements, 409 were present in the post-processed microarray data set from 21 bladder carcinomas and 5 normal bladder mucosa samples. The median expression levels of 226 of these genes were down-regulated across the panel of tumor samples relative to normal bladder mucosa. Among the first 130 array elements, nearly 100 contained a CpG island located around their transcription start sites (Table 4).

TABLE 4

| Gene symbol | Gene name | Ensembl GeneID | Cytoband |
| --- | --- | --- | --- |
| HBA1\|HBA2 | hemoglobin, alpha 1\|hemoglobin, alpha 2 | ENSG00000188536\| ENSG00000130656 | 16p13.3 |
| FBLN2 | fibulin 2 | null | 3p25.1 |
| PRKAR2B | protein kinase, cAMP-dependent, regulatory, type II, beta | ENSG00000005249 | 7q22 |
| RBP7 | retinol binding protein 7, cellular | ENSG00000162444 | 1p36.22 |
| CLU | clusterin (complement lysis inhibitor, SP-40,40, sulfated glycoprotein 2, testosterone-repressed prostate message 2, apolipoprotein J) | ENSG00000120885 | 8p21-p12 |

TABLE 4-continued

| Gene symbol | Gene name | Ensembl GeneID | Cytoband |
|---|---|---|---|
| DDX43 | DEAD (Asp-Glu-Ala-Asp) box polypeptide 43 | ENSG00000080007 | 6q12-q13 |
| C16orf45 | chromosome 16 open reading frame 45 | ENSG00000166780 | 16p13.11 |
| RIMS3 | regulating synaptic membrane exocytosis 3 | ENSG00000117016 | 1pter-p22.2 |
| NGFRAP1L1 | NGFRAP1-like 1 | ENSG00000184515 | Xq22.1 |
| LOC81558 | null | ENSG00000121104 | 17q21.33 |
| CRLF1 | cytokine receptor-like factor 1 | ENSG00000006016 | 19p12 |
| GAGE4|GAGE3| LOC286408|GAGE8| GAGE6|GAGE2|GAGE5| GAGE7B | G antigen 4|G antigen 3|G antigen 8|G antigen 6|G antigen 2|G antigen 5|G antigen 7B | ENSG00000068990| ENSG00000189064 | Xp11.4-p11.2 |
| GAGE1 | G antigen 1 | null | Xp11.4-p11.2 |
| ASMTL | acetylserotonin O-methyltransferase-like | ENSG00000169093 | Xp22.3; Yp11.3 |
| HSPA2 | heat shock 70 kDa protein 2 | ENSG00000126803 | 14q24.1 |
| RND1 | Rho family GTPase 1 | ENSG00000172602 | 12q12-q13 |
| MAPK8IP1 | mitogen-activated protein kinase 8 interacting protein 1 | ENSG00000121653 | 11p12-p11.2 |
| MGC20983 | null | ENSG00000198003 | 19p13.2 |
| KIF5C | kinesin family member 5C | ENSG00000168280 | 2q23.1 |
| NR4A1 | nuclear receptor subfamily 4, group A, member 1 | ENSG00000123358 | 12q13 |
| PCDH10 | protocadherin 10 | null | 4q28.3 |
| UCHL1 | ubiquitin carboxyl-terminal esterase L1 (ubiquitin thiolesterase) | ENSG00000154277 | 4p14 |
| GFPT2 | glutamine-fructose-6-phosphate transaminase 2 | ENSG00000131459 | 5q34-q35 |
| FLJ10324 | null | ENSG00000157927 | 7p22.1 |
| SORBS1 | sorbin and SH3 domain containing 1 | ENSG00000095637 | 10q23.3-q24.1 |
| MAP6 | microtubule-associated protein 6 | ENSG00000171533 | 11q13.3 |
| GPR124 | G protein-coupled receptor 124 | ENSG00000020181 | 8p12 |
| LMCD1 | LIM and cysteine-rich domains 1 | ENSG00000071282 | 3p26-p24 |
| NEFH | neurofilament, heavy polypeptide 200 kDa | ENSG00000100285 | 22q12.2 |
| SNAP25 | synaptosomal-associated protein, 25 kDa | ENSG00000132639 | 20p12-p11.2 |
| C2orf23 | chromosome 2 open reading frame 23 | ENSG00000068615 | 2p11.2 |
| LHX6 | LIM homeobox 6 | ENSG00000106852 | 9q33.2 |
| CCND2 | cyclin D2 | ENSG00000118971 | 12p13 |
| LOC387763 | null | ENSG00000187479 | 11p11.2 |
| CKB | creatine kinase, brain | ENSG00000166165 | 14q32 |
| STXBP1 | syntaxin binding protein 1 | ENSG00000136854 | 9q34.1 |
| C1QL1 | complement component 1, q subcomponent-like 1 | ENSG00000131094 | 17q21 |
| TMEFF2 | transmembrane protein with EGF-like and two follistatin-like domains 2 | ENSG00000144339 | 2q32.3 |
| FZD4 | frizzled homolog 4 (*Drosophila*) | ENSG00000174804 | 11q14.2 |
| ELOVL4 | elongation of very long chain fatty acids (FEN1/Elo2, SUR4/Elo3, yeast)-like 4 | ENSG00000118402 | 6q14 |
| TMOD1 | tropomodulin 1 | ENSG00000136842 | 9q22.3 |
| LCN2 | lipocalin 2 (oncogene 24p3) | ENSG00000148346 | 9q34 |
| TSPAN9 | tetraspanin 9 | null | 12p13.33-p13.32 |
| TESK2 | testis-specific kinase 2 | ENSG00000070759 | 1p32 |
| GAMT | guanidinoacetate N-methyltransferase | ENSG00000130005 | 19p13.3 |
| INHBB | inhibin, beta B (activin AB beta polypeptide) | ENSG00000163083 | 2cen-q13 |
| RGL1 | ral guanine nucleotide dissociation stimulator-like 1 | ENSG00000143344 | 1q25.3 |
| BIRC3 | baculoviral IAP repeat-containing 3 | ENSG00000023445 | 11q22 |
| FKBP7 | FK506 binding protein 7 | ENSG00000079150 | 2q31.2 |
| TCN2 | transcobalamin II; macrocytic anemia | ENSG00000185339 | 22q12.2 |
| LAT2 | linker for activation of T cells family, member 2 | ENSG00000086730 | 7q11.23 |
| STAT4 | signal transducer and activator of transcription 4 | ENSG00000138378 | 2q32.2-q32.3 |
| WBSCR16 | Williams-Beuren syndrome chromosome region 16 | ENSG00000197736| ENSG00000197477 | 7q11.23 |
| IL32 | interleukin 32 | ENSG00000008517 | 16p13.3 |
| HEY1 | hairy/enhancer-of-split related with YRPW motif 1 | ENSG00000164683 | 8q21 |
| MAPT | microtubule-associated protein tau | ENSG00000186868 | 17q21.1 |
| CXCR4 | chemokine (C—X—C motif) receptor 4 | null | 2q21 |
| COL9A2 | collagen, type IX, alpha 2 | ENSG00000049089 | 1p33-p32 |
| RASSF2 | Ras association (RalGDS/AF-6) domain family 2 | ENSG00000101265 | 20pter-p12.1 |
| PTGS1 | prostaglandin-endoperoxide synthase 1 (prostaglandin G/H synthase and cyclooxygenase) | ENSG00000095303 | 9q32-q33.3 |
| AZGP1 | alpha-2-glycoprotein 1, zinc | ENSG00000160862 | 7q22.1 |
| FOS | v-fos FBJ murine osteosarcoma viral oncogene homolog | ENSG00000170345 | 14q24.3 |
| KCNH2 | potassium voltage-gated channel, subfamily H (eag-related), member 2 | ENSG00000055118 | 7q35-q36 |
| CRYM | crystallin, mu | ENSG00000103316 | 16p13.11-p12.3 |
| CGNL1 | cingulin-like 1 | ENSG00000128849 | 15q21.3 |
| NR4A2 | nuclear receptor subfamily 4, group A, member 2 | ENSG00000153234 | 2q22-q23 |
| MYL9 | myosin, light polypeptide 9, regulatory | null | 20q11.23 |
| CX3CL1 | chemokine (C—X3—C motif) ligand 1 | ENSG00000006210 | 16q13 |
| GNAZ | guanine nucleotide binding protein (G protein), alpha z polypeptide | ENSG00000128266 | 22q11.22 |
| RBP1 | retinol binding protein 1, cellular | ENSG00000114115 | 3q23 |
| SELM | null | ENSG00000198832 | 22q12.2 |
| MAP1A | microtubule-associated protein 1A | ENSG00000166963 | 15q13-qter |

TABLE 4-continued

| Gene symbol | Gene name | Ensembl GeneID | Cytoband |
|---|---|---|---|
| TCEAL7 | transcription elongation factor A (SII)-like 7 | ENSG00000182916 | Xq22.1 |
| SERPINF1 | serpin peptidase inhibitor, clade F (alpha-2 antiplasmin, pigment epithelium derived factor), member 1 | ENSG00000132386 | 17p13.1 |
| CRISPLD2 | cysteine-rich secretory protein LCCL domain containing 2 | ENSG00000103196 | 16q24.1 |
| LRRC32 | leucine rich repeat containing 32 | ENSG00000137507 | 11q13.5-q14 |
| RRAD | Ras-related associated with diabetes | ENSG00000166592 | 16q22 |
| HTRA3 | HtrA serine peptidase 3 | ENSG00000170801 | 4p16.1 |
| GEM | GTP binding protein overexpressed in skeletal muscle | ENSG00000164949 | 8q13-q21 |
| CLGN | calmegin | ENSG00000153132 | 4q28.3-q31.1 |
| C9orf58 | chromosome 9 open reading frame 58 | ENSG00000126878 | 9q34.13-q34.3 |
| C20orf100 | chromosome 20 open reading frame 100 | ENSG00000124191 | 20q13.12 |
| C1orf115 | chromosome 1 open reading frame 115 | ENSG00000162817 | 1q41 |
| C9orf61 | chromosome 9 open reading frame 61 | ENSG00000135063 | 9q13-q21 |
| HYAL1 | hyaluronoglucosaminidase 1 | ENSG00000114378 | 3p21.3-p21.2 |
| LOH3CR2A | loss of heterozygosity, 3, chromosomal region 2, gene A | null | 3p24-26 |
| CLEC1A | C-type lectin domain family 1, member A | ENSG00000150048 | 12p13.2 |
| MAPT | microtubule-associated protein tau | null | 17q21.1 |
| PLXNB3 | plexin B3 | null | Xq28 |
| PLAT | plasminogen activator, tissue | ENSG00000104368 | 8p12 |
| EDN2 | endothelin 2 | ENSG00000127129 | 1p34 |
| GSTA4 | glutathione S-transferase A4 | ENSG00000170899 | 6p12.1 |
| VIM | vimentin | ENSG00000026025 | 10p13 |
| SLC2A3 | solute carrier family 2 (facilitated glucose transporter), member 3 | null | 12p13.3 |
| ITGA7 | integrin, alpha 7 | ENSG00000135424 | 12q13 |
| COL6A3 | collagen, type VI, alpha 3 | ENSG00000163359 | 2q37 |
| GDF15 | growth differentiation factor 15 | ENSG00000130513 | 19p13.1-13.2 |
| SLPI | secretory leukocyte peptidase inhibitor | ENSG00000124107 | 20q12 |
| COL5A1 | collagen, type V, alpha 1 | ENSG00000130635 | 9q34.2-q34.3 |
| MPP1 | membrane protein, palmitoylated 1, 55 kDa | ENSG00000130830 | Xq28 |

Methylation Status of Novel Candidate Genes In Vitro and In Vivo

Figure 2:
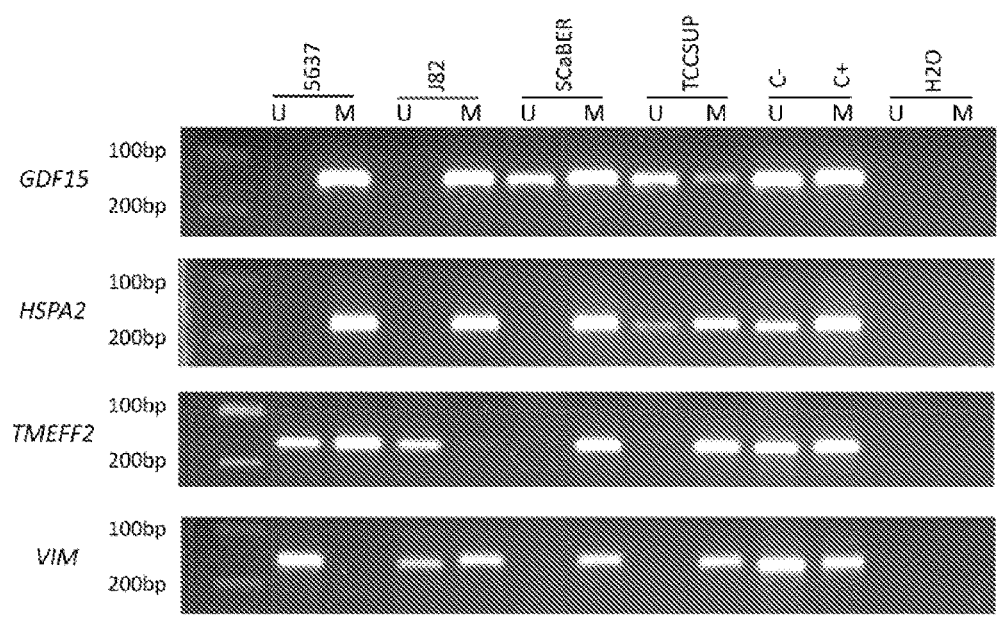
FIG. 2 shows illustrative examples of methylation-specific PCR to analyze DNA methylation status of GDF15, HSPA2, TMEFF2, and VIM in bladder cancer cell lines.

Twenty-one of the DNA methylation candidate genes were analyzed by MSP in BlCa cell lines. The four best performing markers, hypermethylated in at least three cell lines, were selected for further validation: GDF15, HSPA2, TMEFF2 and VIM (summarized in Table 5). With the exception of TMEFF2, the markers were more often methylated in BlCa than in kidney and prostate cancer cell lines. Illustrative examples of MSP results are shown in FIG. 2. Using quantitative MSP (qMSP) GDF15, HSPA2, TMEFF2, and VIM were found to be methylated in 66%, 64%, 48%, and 96% of the bladder tumors, respectively, and in none of the normal urothelium (Table 6). Differences in quantitative methylation levels between cancer patients and bladder cancer-free individuals were statistically significant for all genes (Mann-Whitney, P<0.001). Finally, a statistically significant correlation between methylation levels of HSPA2, on the one hand, and TMEFF2 (Spearman's test, r=0.592, P<0.001), and VIM (r=0.506, P<0.001), on the other, was also found.

TABLE 5

Gene promoter methylation status in bladder (BlCa), renal (RCT) and prostate (PCa) cancer cell lines analyzed by methylation-specific PCR (MSP).

| | GDF15 | HSPA2 | TMEFF2 | VIM |
|---|---|---|---|---|
| BlCa cell lines | | | | |
| 5637 | M | M | U/M | U |
| J82 | M | M | U/M | U/M |
| SCaBER | U/M | M | M | M |
| TCCSUP | U/M | U/M | U/M | M |
| RCT cell lines | | | | |
| 786-O | U | U | U/M | U |
| ACHN | M | U | U/M | U |
| Caki-1 | U | U | U/M | U |
| Caki-2 | U | U | U/M | U |
| PCa cell lines | | | | |
| 22Rv1 | U | U | U/M | U/M |
| DU145 | M | U | M | U |
| LNCaP | U/M | M | U/M | U |
| PC-3 | U | U/M | U/M | U |

U, unmethylated;
M, methylated;
U/M, partial methylated

TABLE 6

Frequency and distribution of promoter methylation levels in normal bladder mucosa (NBM) and bladder cancer (BlCa) tissue samples measured by quantitative methylation-specific PCR (qMSP).

Figure 3:
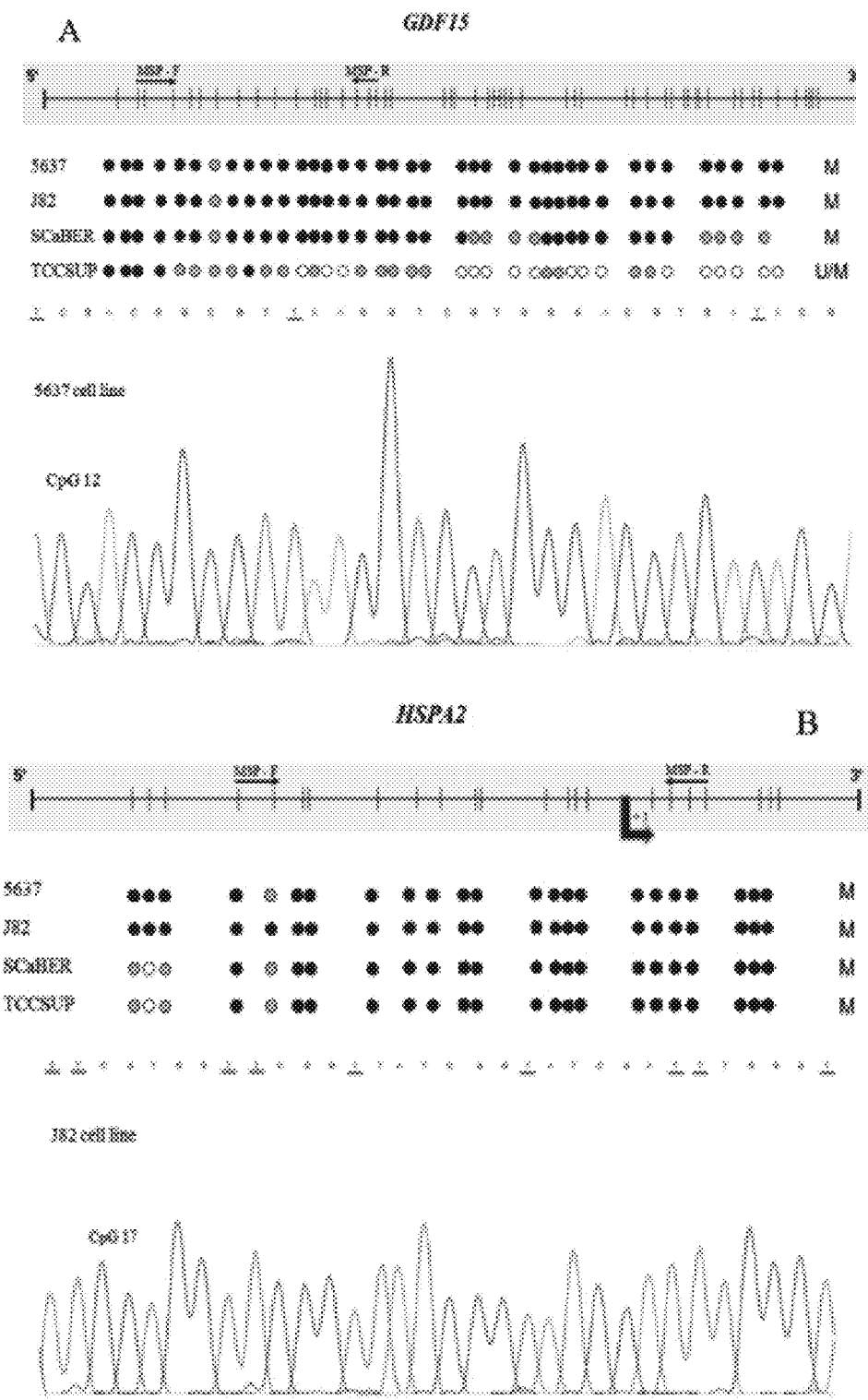
FIG. 3 shows characterization of the methylation status of individual CpG dinucleotides by bisulfite sequencing of the GDF15 (A), HSPA2 (B), TMEFF2 (C), and VIM (D). The upper part of each panel provides a schematic representation of the CpG island in the area of the transcription start (+1). Vertical bars indicate the location of individual CpG sites and the two arrows indicate a location of methylation-specific PCR (MSP) primers. For the middle part of each panel, unfilled circles represent unmethylated CpGs, black filled circles represent methylated CpGs and grey filled circles represent partially methylated sites in the respective bladder cancer cell lines. The column of U, M and U/M, at the right side, lists the methylation status of the cell line from MSP analysis of the corresponding gene. The lower panel is a section of the bisulfite sequence electropherogram, where cytosines in CpG sites are indicated and cytosines that have been converted to thymines are underlined.
Figure 3:
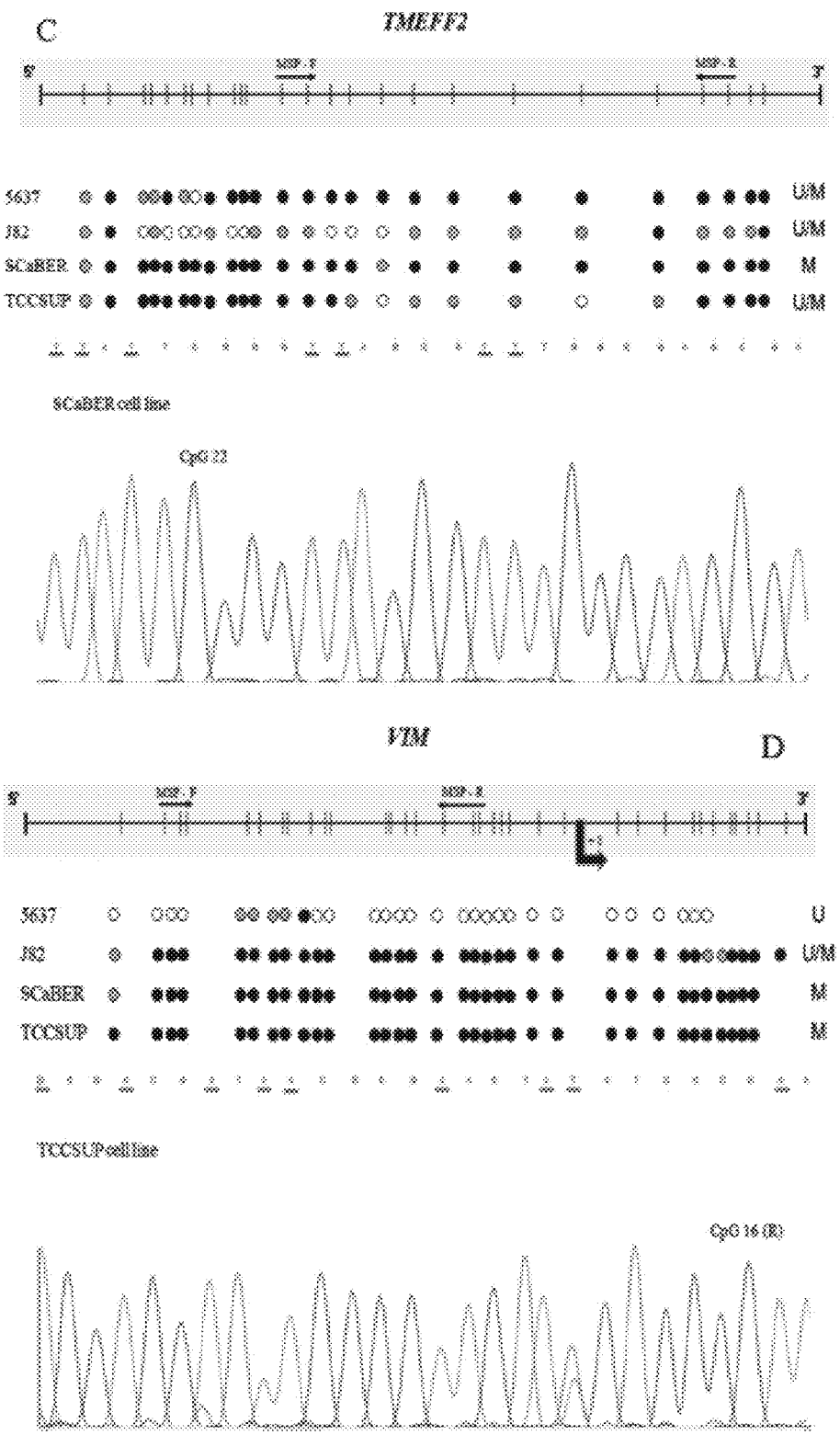

| Gene | NBM, n | NBM med (IQR) | Bl Ca, n | BlCa med (IQR) | P value* |
|------|--------|---------------|----------|----------------|----------|
| GDF15 | 0/20 | 4.35 (1.22-16.82) | 33/50 | 219.39 (13.82-480.80) | <0.001 |
| HSPA2 | 0/20 | 1.14 (0.76-1.91) | 32/50 | 31.79 (3.02-184.58) | <0.001 |
| TMEFF2 | 0/20 | 0.38 (0.08-1.41) | 24/50 | 10.89 (1.32-143.74) | <0.001 |
| VIM | 0/20 | 0.0 (0.0-0.0) | 48/50 | 237.15 (94.22-466.59) | <0.001 | n, number of positive cases;
med, median;
IQR, interquartile range;
*Mann-Whitney test Bisulfite Sequencing Verification of Promoter Methylation Status To verify the promoter methylation status assessed by MSP, GDF15, HSPA2, TMEFF2 and VIM were subjected to bisulfite sequencing in BlCa cell lines (FIG. 3). In general, after age-matching between BlCa patients and controls. As expected, high tumor grade and stage were significantly associated with shorter overall survival (log-rank, P<0.001). However, methylation levels were not predictive of outcome.

TABLE 7

Distribution of methylation levels among bladder cancer tissues according to histopathological grade and stage.

| | GDF15 Med (IQR) | HSPA2 Med (IQR) | TMEFF2 Med (IQR) | VIM Med (IQR) |
|---|---|---|---|---|
| Grade | | | | |
| Papillary, low grade | 361.61 (27.45-515.53) | 3.04 (1.02-73.29) | 2.11 (0.0-10.35) | 171.86 (36.63-336.65) |
| Papillary, high grade | 261.50 (97.65-505.41) | 49.64 (7.63-224.0) | 45.73 (1.74-149.64) | 315.34 (142.79-493.25) |
| Invasive, high grade | 105.10 (1.84-185.82) | 168.38 (42.19-297.92) | 240.0 (64.63-285.13) | 254.90 (219.68-373.78) |
| P value* | 0.226 | 0.032 | 0.005 | 0.152 |
| Stage | | | | |
| pTa | 394.54 (132.77-681.07) | 4.35 (0.95-29.10) | 3.21 (0.0-12.42) | 234.53 (41.10-380.05) |
| pT1 | 382.68 (3.79-483.79) | 58.43 (3.04-185.74) | 9.35 (1.18-160.83) | 230.46 (80.74-431.78) |
| pT2/pT4 | 127.21 (1.86-159.21) | 145.51 (37.40-274.51) | 90.98 (33.38-243.56) | 254.46 (169.62-478.40) |
| P value* | 0.050 | 0.062 | 0.026 | 0.904 | n, number of positive cases;
Med, median;
IQR, interquartile range;
*Kruskal-Wallis test CpG island methylation patterns observed by bisulfite sequencing correlated well with the MSP scoring data.

Figure 4:
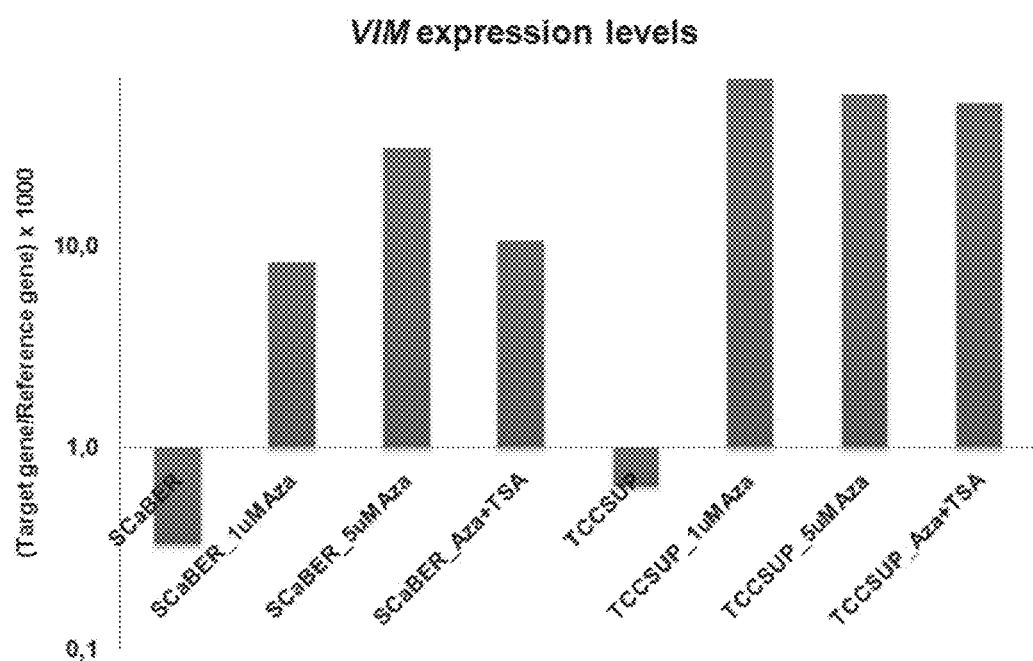
FIG. 4 shows VIM promoter methylation and mRNA expression levels in bladder cancer cell lines after pharmacological treatment with the demethylating 5-aza-2'deoxycytidine alone (1 μM and 5 μM) and in combination with the deacetylase inhibitor trichostatin A (0.5 μM). Below each sample the respective methylation status is shown, as assessed by methylation-specific PCR. Black circles represent promoter methylation of the genes and grey circles represent the presence of both unmethylated and methylated alleles.

Association Between CpG Island Hypermethylation and Transcriptional Gene Silencing in Bladder Cancer Cell Lines Bladder cancer cell lines hypermethylated for GDF15, HSPA2, TMEFF2 and VIM showed low transcript expression, which restored or increased after promoter demethylation induced either by 1 μM or 5 μM of 5-aza-dC alone, or by the combined treatment with 5-aza-dC and TSA (illustrated for VIM in FIG. 4). Overall, these results show a correlation between promoter methylation and decreased gene expression levels.

Figure 5:
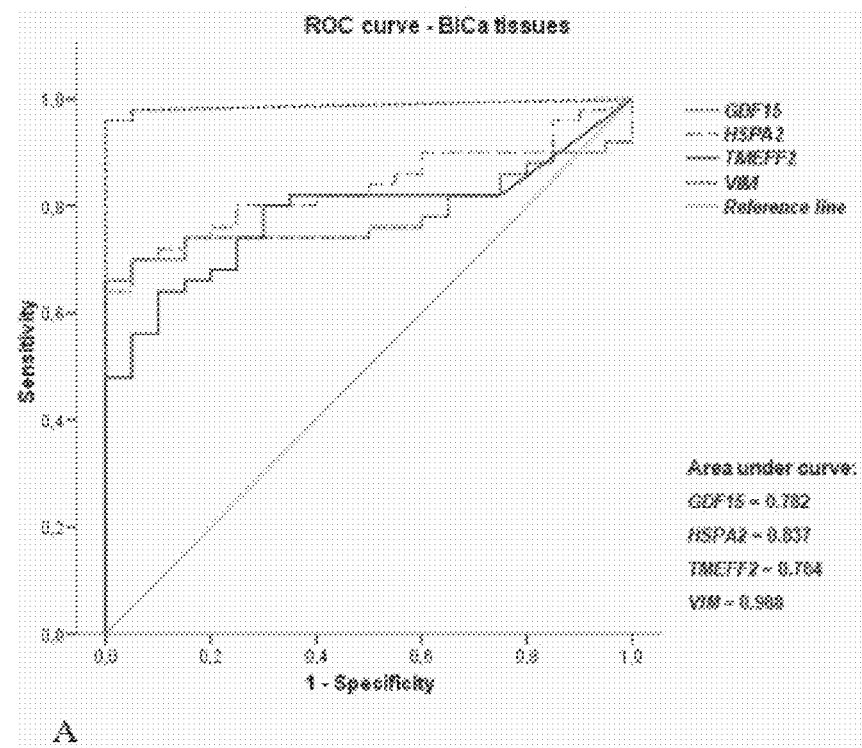
FIG. 5 shows the receiver operating characteristic (ROC) curve in bladder cancer tissue and normal tissue based on A) GDF15, HSPA2, TMEFF2, and VIM individually and B) GDF15, TMEFF2, and VIM combined
Figure 5:
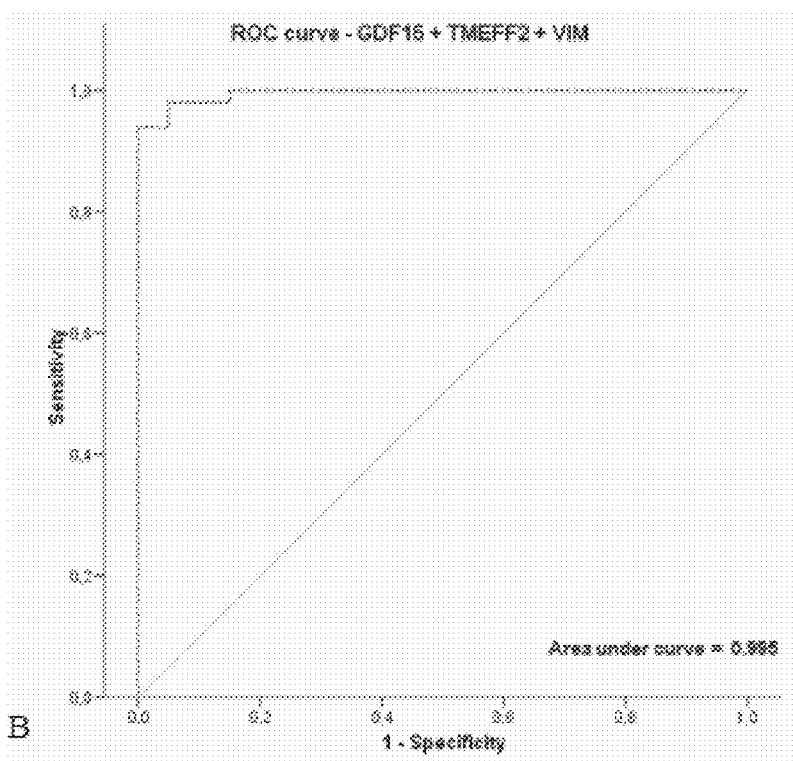

Association Between Quantitative Promoter Methylation Levels and Clinicopathological Variables in Primary Tumors Relationship between methylation status and clinicopathological variables of BlCa patients is summarized in Table 7. With the exception of GDF15, high-grade, muscle-invasive tumors displayed higher methylation levels than superficial low-grade tumors. A significant association of methylation levels with increasing tumor grade and stage was found for TMEFF2 (Kruskal-Wallis, P=0.005 and P=0.026, respectively), and with tumor grade for HSPA2 (P=0.032). No statistically significant association was found between gene promoter methylation and patient's age, even Evaluation of the biomarkers diagnostic potential using tissue and urine samples Among the possible gene combinations tested, three gene methylation markers—GDF15, TMEFF2, and VIM—demonstrated superior performance in terms of sensitivity and specificity for discriminating BlCa patients from controls (Table 8). Remarkably, a sensitivity of 100% (17/17) was apparent for early-stage Ta and low-grade BlCa. The ROC curve based on these epi-markers (FIG. 5) resulted in an area under the curve (AUC) of 0.995, with a 95% confidence interval (CI) of 0.985-1.000, at a significance of P<0.001. Equal sensitivity and specificity rates were obtained with the four-gene panel.

TABLE 8

Performance of epi-markers for bladder cancer (BlCa) in tissue and urine sediments (HD, healthy donors; RCT, renal cell tumor patients; PCa, prostate carcinoma patients).

| | Sensitivity % (n positive/n total) | Specificity % (n negative/n total) | PPV % | NPV % |
|---|---|---|---|---|
| Tissue samples | | | | |
| VIM | 96 (48/50) | 100 (20/20) | 100 | 91 |
| VIM/TMEFF2 | 98 (49/50) | 100 (20/20) | 100 | 95 |

TABLE 8-continued

Performance of epi-markers for bladder cancer (BlCa) in tissue and urine sediments (HD, healthy donors; RCT, renal cell tumor patients; PCa, prostate carcinoma patients).

|  | Sensitivity % (n positive/n total) | Specificity % (n negative/n total) | PPV % | NPV % |
|---|---|---|---|---|
| VIM/TMEFF2/GDF15 | 100 (50/50) | 100 (20/20) | 100 | 100 |
| VIM/TMEFF2/GDF15/HSPA2 | 100 (50/50) | 100 (20/20) | 100 | 100 |
| Urine samples (BlCa vs. HD) | | | | |
| VIM | 78 (40/51) | 100 (20/20) | 100 | 64 |
| VIM/TMEFF2 | 82 (42/51) | 100 (20/20) | 100 | 69 |
| VIM/TMEFF2/GDF15 | 94 (48/51) | 100 (20/20) | 100 | 87 |
| VIM/TMEFF2/GDF15/HSPA2 | 94 (48/51) | 100 (20/20) | 100 | 87 |
| Urine samples (BlCa vs. HD, RCT and PCa) | | | | |
| VIM | 78 (40/51) | 97 (57/59) | 95 | 84 |
| VIM/TMEFF2 | 82 (42/51) | 95 (56/59) | 93 | 86 |
| VIM/TMEFF2/GDF15 | 94 (48/51) | 90 (53/59) | 89 | 95 |
| VIM/TMEFF2/GDF15/HSPA2 | 94 (48/51) | 86 (51/59) | 86 | 94 |

PPV—positive predictive value;
NPV, negative predictive value

In an independent training set of urine sediments from non-cancerous donors, bladder cancer, renal cell carcinoma, and prostate cancer patients' methylation levels were found to be significantly higher in urine from bladder cancer patients compared to normal samples from non-cancerous donors for all genes (Table 9; Mann-Whitney, $P<0.001$). The differences in methylation levels in urine samples from bladder cancer patients and from other urological tumors was also statistically significant ($P<0.001$). Moreover, a statistically significant correlation was found between methylation levels of HSPA2 and TMEFF2 (Spearman's test, $r=0.638$, $P<0.001$) and VIM ($r=0.546$, $P<0.001$), as well as between VIM levels and GDF15 ($r=0.289$, $P=0.040$) and TMEFF2 methylation levels ($r=0.598$, $P<0.001$).

Figure 6:
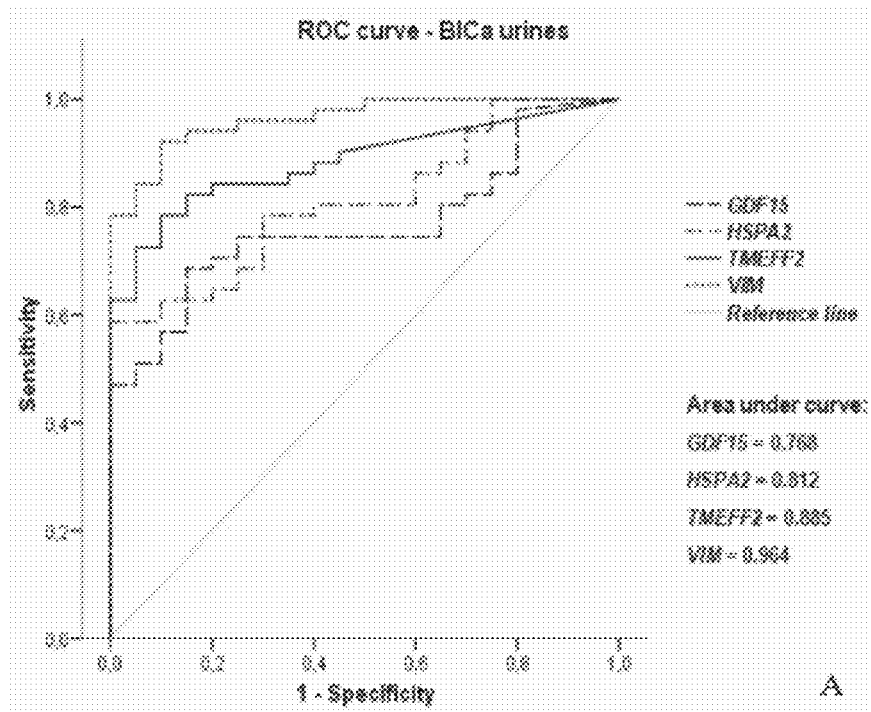
FIG. 6 shows receiver operating characteristic curve in bladder cancer urines for each individual gene (GDF15, HSPA2, TMEFF2, and VIM) (A) and the combination of three genes (GDF15, TMEFF2, and VIM) (B).
Figure 6:
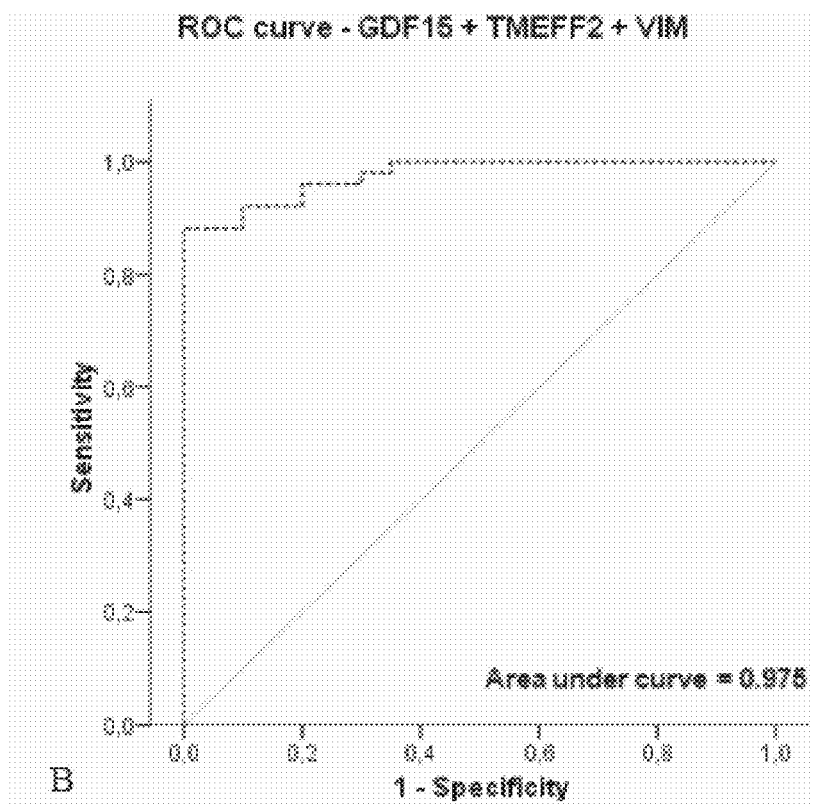
Figure 7:
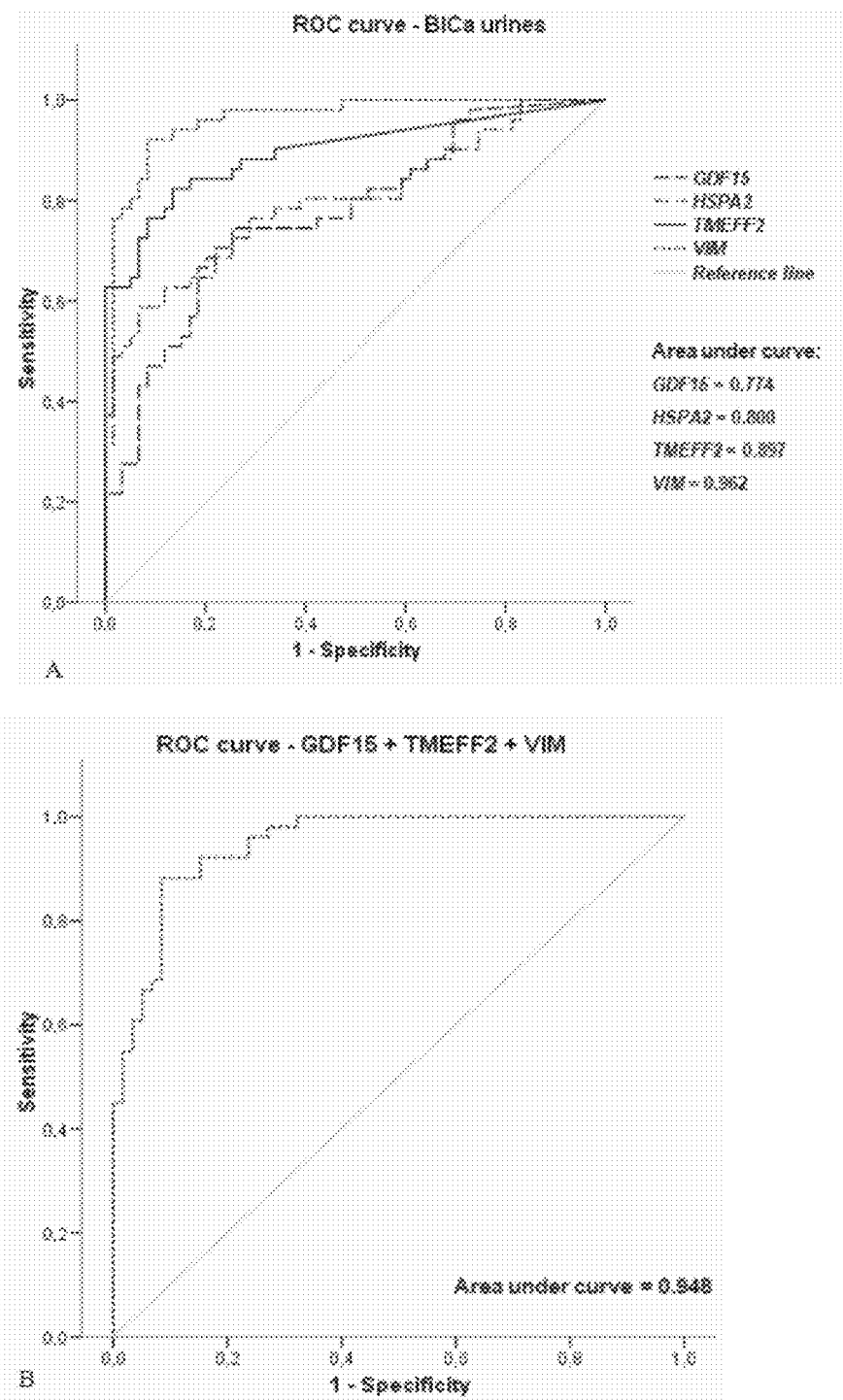
FIG. 7 shows ROC curves for each individual gene (GDF15, HSPA2, TMEFF2, and VIM) (A) and the combination of three genes (GDF15, TMEFF2, and VIM) (B) where sets of healthy donors and other urological cancers were combined to constitute the control group.

Interestingly, the relative methylation levels of the genes tested were not significantly different among non-cancerous donors, renal cell tumor and prostate cancer patients, except for GDF15 levels that differed between donors and renal cell tumor ($P=0.009$). The same three-gene panel displaying the best performance for detecting BlCa in tissue samples demonstrated a sensitivity of 94% (48/51) and a specificity of 100% (20/20) for BlCa detection in urine samples (Table 8). ROC curve analysis showed an AUC of 0.975 (95% CI, 0.948-1.000, $P<0.001$) (FIG. 6). Moreover, when the sets of healthy donors and other urological cancers were combined to constitute the control group, the specificity rate decreased slightly (90%), displaying an AUC of 0.948 (95% CI, 0.912-0.985, $P<0.001$) (FIG. 7).

Thirty-one out of the 51 (61%) BlCa urines were examined by an experienced cytopathologist. Thirteen cases were cytologically diagnosed as malignant (three were low grade), eight as negative for malignancy, and 10 cases were "inconclusive/suspicious for malignancy". Remarkably, the three-gene panel correctly identified as BlCa the 13 malignant cases and the 8 negative cases diagnosed by cytology, as well as nine out of the ten "inconclusive/suspicious" cases. Moreover, of the 17 low grade BlCa, only one was missed by the three-gene panel in urine sediments.

Of the 51 BlCa urine samples tested, 12 were from cases in which the corresponding tissue sample was analysed in the preceding experiments. Although not all individual gene promoters methylated in tissue samples were correspondingly detected in urine, full concordance was seen for the three-gene epi-biomarker panel (GDF15, TMEFF2, and VIM) (Table 10).

TABLE 10

Distribution of promoter methylation of GDF15, TMEFF2 and VIM across matched bladder tumor and urine samples from the same patient. A filled box indicates a hypermethylated gene, whereas a blank box corresponds to an unmethylated gene. Samples were considered methylation positive when the ratio was higher than the highest value of the respective normal samples.

| Patient | Sample | GDF15 | TMEFF2 | VIM | Methylation status |
|---|---|---|---|---|---|
| #1 | Tissue | X |  | X | Positive |
|  | Urine | X | X | X | Positive |

TABLE 9

Frequency and distribution of promoter methylation levels in urine sediments collected from healthy donors (HD), and bladder (BlCa), renal (RCT) and prostate (PCa) cancer patients. Samples were scored as methylation positive when the value/PMR was higher than the highest value across the respective normal healthy donors. The p-value refers to the statistical comparison with BlCa.

|  |  | GDF15 | HSPA2 | TMEFF2 | VIM |
|---|---|---|---|---|---|
| BlCa | Freq. methylation | 24/51 | 30/51 | 32/51 | 40/51 |
|  | med (IQR) | 9.34 (2.50-33.12) | 8.15 (2.52-71.84) | 4.63 (1.10-40.37) | 45.47 (7.50-254.48) |
| HD | Freq. methylation | 0/20 | 0/20 | 0/20 | 0/20 |
|  | med (IQR) | 1.64 (0.68-3.53) | 1.54 (0.25-3.02) | 0.0 (0.0-0.51) | 0.25 (0.0-1.40) |
|  | P value* | <0.001 | <0.001 | <0.001 | <0.001 |
| RCT | Freq. methylation | 1/19 | 2/19 | 2/19 | 1/19 |
|  | med (IQR) | 0.32 (0.0-1.07) | 1.78 (0.64-2.72) | 0.0 (0.0-0.22) | 0.24 (0.0-0.45) |
|  | P value* | <0.001 | <0.001 | <0.001 | <0.001 |
| PCa | Freq. methylation | 4/20 | 3/20 | 0/20 | 1/20 |
|  | med (IQR) | 1.08 (0.36-9.72) | 1.46 (0.37-2.71) | 0.0 (0.0-0.14) | 0.0 (0.0-0.38) |
|  | P value* | 0.012 | <0.001 | <0.001 | <0.001 | med, median;
IQR, interquartile range;
*Mann-Whitney test;

TABLE 10-continued

Distribution of promoter methylation of GDF15, TMEFF2 and VIM across matched bladder tumor and urine samples from the same patient. A filled box indicates a hypermethylated gene, whereas a blank box corresponds to an unmethylated gene. Samples were considered methylation positive when the ratio was higher than the highest value of the respective normal samples.

| Patient | Sample | GDF15 | TMEFF2 | VIM | Methylation status |
|---|---|---|---|---|---|
| #2 | Tissue | X | X | X | Positive |
|    | Urine |   | X | X | Positive |
| #3 | Tissue | X |   | X | Positive |
|    | Urine | X |   | X | Positive |
| #4 | Tissue |   | X | X | Positive |
|    | Urine |   | X |   | Positive |
| #5 | Tissue | X | X | X | Positive |
|    | Urine |   | X | X | Positive |
| #6 | Tissue | X |   | X | Positive |
|    | Urine | X |   |   | Positive |
| #7 | Tissue | X | X | X | Positive |
|    | Urine | X | X | X | Positive |
| #8 | Tissue | X | X | X | Positive |
|    | Urine |   | X | X | Positive |
| #9 | Tissue | X |   | X | Positive |
|    | Urine |   |   | X | Positive |
| #10 | Tissue |   | X |   | Positive |
|     | Urine |   | X | X | Positive |
| #11 | Tissue |   | X | X | Positive |
|     | Urine |   | X | X | Positive |
| #12 | Tissue | X | X | X | Positive |
|     | Urine | X | X | X | Positive |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the medical sciences are intended to be within the scope of the following claims.

The invention claimed is:

1. A method for detecting the methylation of a target nucleic acid segment in a urine sample from a subject comprising:
   a) treating nucleic acid from said urine sample from said subject with sodium bisulfite to provide bisulfite modified nucleic acid and contacting said bisulfite-modified nucleic acid with a methylation-specific oligonucleotide primer pair for amplification of a target nucleic acid segment containing CpG islands from the VIM promoter region, wherein the subject has been previously diagnosed with bladder cancer or has been identified as being at risk of having or developing bladder cancer; and
   b) amplifying said target nucleic acid segment from the VIM promoter region with said methylation-specific oligonucleotide primer pair to provide amplified target nucleic acid.

2. The method of claim 1, further comprising detecting the methylation of at least one target nucleic acid segment having CpG islands from a promoter region selected from the group consisting of the GDF15 promoter region, HSPA2 promoter region, and TMEFF2 promoter region in said urine sample from said subject by a) additionally contacting said bisulfite-modified nucleic acid with at least one methylation-specific oligonucleotide primer pair for amplification of said at least one target nucleic acid segment having CpG islands from a promoter region selected from the group consisting of the GDF15 promoter region, HSPA2 promoter region, and TMEFF2 promoter region and b) amplifying the at least one target nucleic acid segment having CpG islands from a promoter region selected from the group consisting of the GDF15 promoter region, HSPA2 promoter region, and TMEFF2 promoter region with said at least one methylation-specific oligonucleotide primer pair to provide amplified target nucleic acid.

3. The method of claim 1, further comprising detecting at least two nucleic acid segments having CpG islands from a promoter region selected from the group consisting of the GDF15 promoter region, HSPA2 promoter region, and TMEFF2 promoter region in said urine sample from said subject by a) additionally contacting said bisulfite-modified nucleic acid with at least two methylation-specific oligonucleotide primer pairs for amplification of said at least two target nucleic acid segments having CpG islands from a promoter region selected from the group consisting of the GDF15 promoter region, HSPA2 promoter region, and TMEFF2 promoter region and b) amplifying the at least two target nucleic acid segments having CpG islands from a promoter region selected from the group consisting of the GDF15 promoter region, HSPA2 promoter region, and TMEFF2 promoter region with said at least two methylation-specific oligonucleotide primer pairs to provide amplified target nucleic acid.

4. The method of claim 1, further comprising detecting target nucleic acid segments having CpG islands from GDF15, HSPA2 and TMEFF2 promoter regions in said urine sample from said subject by a) additionally contacting said bisulfite-modified nucleic acid with three methylation-specific oligonucleotide primer pairs for amplification of said target nucleic acid segments having CpG islands from said GDF15, HSPA2 and TMEFF2 promoter regions and b) amplifying the target nucleic acid segments having CpG islands from said GDF15, HSPA2 and TMEFF2 promoter regions with said three methylation-specific oligonucleotide primer pairs to provide amplified target nucleic acid.

* * * * *

SEQUENCE LISTING

```
<160> NUMBER OF SEQ ID NOS: 42

<210> SEQ ID NO 1
<211> LENGTH: 23
<212> TYPE: DNA
<213> ORGANISM: Artificial Sequence
<220> FEATURE:
<223> OTHER INFORMATION: Synthetic

<400> SEQUENCE: 1
atttggtggt tatttgtatt tgt                                            23

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
aacaatcata tcacatccca ca                                             22

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
cggcggttat ttgtatttgc                                                20

<210> SEQ ID NO 4
<211> LENGTH: 19
<212> TYPE: DNA
<213> ORGANISM: Artificial Sequence
```

```
<220> FEATURE:
<223> OTHER INFORMATION: Synthetic

<400> SEQUENCE: 4
aacgatcgta tcacgtccc                                                   19

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
ttataagaat tgggaattgg gt                                               22

<210> SEQ ID NO 6
<211> LENGTH: 21
<212> TYPE: DNA
<213> ORGANISM: Artificial Sequence
<220> FEATURE:
<223> OTHER INFORMATION: Synthetic

<400> SEQUENCE: 6
aaatcaatac caataaccaa a                                                21

<210> SEQ ID NO 7
<211> LENGTH: 19
<212> TYPE: DNA
<213> ORGANISM: Artificial Sequence
<220> FEATURE:
<223> OTHER INFORMATION: Synthetic

<400> SEQUENCE: 7
taagaatcgg gaattgggc                                                   19

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
aatcgatacc gataaccgaa                                                  20

<210> SEQ ID NO 9
<211> LENGTH: 18
<212> TYPE: DNA
<213> ORGANISM: Artificial Sequence
<220> FEATURE:
<223> OTHER INFORMATION: Synthetic

<400> SEQUENCE: 9
ggaagagggg tgttagtt                                                    18

<210> SEQ ID NO 10
<211> LENGTH: 21
<212> TYPE: DNA
<213> ORGANISM: Artificial Sequence
<220> FEATURE:
<223> OTHER INFORMATION: Synthetic

<400> SEQUENCE: 10
aacactaacc caaataaaac t                                                21
```

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
gaagaggggc gttagttc                                                 18

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
acgctaaccc gaataaaact                                               20

<210> SEQ ID NO 13
<211> LENGTH: 25
<212> TYPE: DNA
<213> ORGANISM: Artificial Sequence
<220> FEATURE:
<223> OTHER INFORMATION: Synthetic

<400> SEQUENCE: 13
gggttataaa aatagtgttt ttggt                                         25

<210> SEQ ID NO 14
<211> LENGTH: 23
<212> TYPE: DNA
<213> ORGANISM: Artificial Sequence
<220> FEATURE:
<223> OTHER INFORMATION: Synthetic

<400> SEQUENCE: 14
acaataacac aaactaactc cca                                           23

<210> SEQ ID NO 15
<211> LENGTH: 22
<212> TYPE: DNA
<213> ORGANISM: Artificial Sequence
<220> FEATURE:
<223> OTHER INFORMATION: Synthetic

<400> SEQUENCE: 15
ttataaaaat agcgttttcg gc                                            22

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
ataacgcgaa ctaactcccg                                               20

<210> SEQ ID NO 17
<211> LENGTH: 22
<212> TYPE: DNA
<213> ORGANISM: Artificial Sequence
<220> FEATURE:
<223> OTHER INFORMATION: Synthetic

<400> SEQUENCE: 17
tgtgggtgat tagttttttt at                                                22

<210> SEQ ID NO 18
<211> LENGTH: 18
<212> TYPE: DNA
<213> ORGANISM: Artificial Sequence
<220> FEATURE:
<223> OTHER INFORMATION: Synthetic

<400> SEQUENCE: 18
acccaaccca aatcttcc                                                     18

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
gtaagtttgt ggtggagttg                                                   20

<210> SEQ ID NO 20
<211> LENGTH: 23
<212> TYPE: DNA
<213> ORGANISM: Artificial Sequence
<220> FEATURE:
<223> OTHER INFORMATION: Synthetic

<400> SEQUENCE: 20
aatctccacc ttaccatatt aaa                                               23

<210> SEQ ID NO 21
<211> LENGTH: 21
<212> TYPE: DNA
<213> ORGANISM: Artificial Sequence
<220> FEATURE:
<223> OTHER INFORMATION: Synthetic

<400> SEQUENCE: 21 ttattttag ttyggagaga c                                                  21

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
gaaaaccaca aataaactcr                                                   20

<210> SEQ ID NO 23
<211> LENGTH: 16
<212> TYPE: DNA
<213> ORGANISM: Artificial Sequence
<220> FEATURE:
<223> OTHER INFORMATION: Synthetic

<400> SEQUENCE: 23
ggttgggatg gtagtg                                                       16

<210> SEQ ID NO 24

```
<211> LENGTH: 19
<212> TYPE: DNA
<213> ORGANISM: Artificial Sequence
<220> FEATURE:
<223> OTHER INFORMATION: Synthetic

<400> SEQUENCE: 24
gtaactccra ctaaaactc                                                 19

<210> SEQ ID NO 25
<211> LENGTH: 25
<212> TYPE: DNA
<213> ORGANISM: Artificial Sequence
<220> FEATURE:
<223> OTHER INFORMATION: Synthetic

<400> SEQUENCE: 25
tggtgatgga ggaggtttag taagt                                          25

<210> SEQ ID NO 26
<211> LENGTH: 27
<212> TYPE: DNA
<213> ORGANISM: Artificial Sequence
<220> FEATURE:
<223> OTHER INFORMATION: Synthetic

<400> SEQUENCE: 26
aaccaataaa acctactcct cccttaa                                        27

<210> SEQ ID NO 27
<211> LENGTH: 30
<212> TYPE: DNA
<213> ORGANISM: Artificial Sequence
<220> FEATURE:
<223> OTHER INFORMATION: Synthetic

<400> SEQUENCE: 27
accaccaccc aacacacaat aacaaacaca                                     30

<210> SEQ ID NO 28
<211> LENGTH: 36
<212> TYPE: DNA
<213> ORGANISM: Artificial Sequence
<220> FEATURE:
<223> OTHER INFORMATION: Synthetic

<400> SEQUENCE: 28
ggttaggtat agtggtttat atttgtaatt ttagta                              36

<210> SEQ ID NO 29
<211> LENGTH: 33
<212> TYPE: DNA
<213> ORGANISM: Artificial Sequence
<220> FEATURE:
<223> OTHER INFORMATION: Synthetic

<400> SEQUENCE: 29
attaactaaa ctaatcttaa actcctaacc tca                                 33

<210> SEQ ID NO 30
<211> LENGTH: 16
<212> TYPE: DNA
<213> ORGANISM: Artificial Sequence
<220> FEATURE:
<223> OTHER INFORMATION: Synthetic

<400> SEQUENCE: 30
```
cctaccttaa cctccc                                                    16

<210> SEQ ID NO 31
<211> LENGTH: 21
<212> TYPE: DNA
<213> ORGANISM: Artificial Sequence
<220> FEATURE:
<223> OTHER INFORMATION: Synthetic

<400> SEQUENCE: 31
tcggcggtta tttgtatttg c                                              21

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
cgtcgaaaac aaccgaaaca                                                20

<210> SEQ ID NO 33
<211> LENGTH: 16
<212> TYPE: DNA
<213> ORGANISM: Artificial Sequence
<220> FEATURE:
<223> OTHER INFORMATION: Synthetic

<400> SEQUENCE: 33
ttttcgaggt ttttcg                                                    16

<210> SEQ ID NO 34
<211> LENGTH: 23
<212> TYPE: DNA
<213> ORGANISM: Artificial Sequence
<220> FEATURE:
<223> OTHER INFORMATION: Synthetic

<400> SEQUENCE: 34
tttcgtttta acgtcgttcg ttt                                            23

<210> SEQ ID NO 35
<211> LENGTH: 23
<212> TYPE: DNA
<213> ORGANISM: Artificial Sequence
<220> FEATURE:
<223> OTHER INFORMATION: Synthetic

<400> SEQUENCE: 35
ccgacgcacg aataaataat acc                                            23

<210> SEQ ID NO 36
<211> LENGTH: 18
<212> TYPE: DNA
<213> ORGANISM: Artificial Sequence
<220> FEATURE:
<223> OTHER INFORMATION: Synthetic

<400> SEQUENCE: 36
tcggttatcg gtatcgat                                                  18

<210> SEQ ID NO 37
<211> LENGTH: 16
<212> TYPE: DNA

```
<213> ORGANISM: Artificial Sequence
<220> FEATURE:
<223> OTHER INFORMATION: Synthetic

<400> SEQUENCE: 37
gttcggggtt acgcgc                                                     16

<210> SEQ ID NO 38
<211> LENGTH: 18
<212> TYPE: DNA
<213> ORGANISM: Artificial Sequence
<220> FEATURE:
<223> OTHER INFORMATION: Synthetic

<400> SEQUENCE: 38
ttcgcctcac tctccgct                                                   18

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
tcggatttcg ttttcggtag                                                 20

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
ttcgggagtt agttcgcgtt                                                 20

<210> SEQ ID NO 41
<211> LENGTH: 19
<212> TYPE: DNA
<213> ORGANISM: Artificial Sequence
<220> FEATURE:
<223> OTHER INFORMATION: Synthetic

<400> SEQUENCE: 41
accgccgaac atcctacga                                                  19

<210> SEQ ID NO 42
<211> LENGTH: 19
<212> TYPE: DNA
<213> ORGANISM: Artificial Sequence
<220> FEATURE:
<223> OTHER INFORMATION: Synthetic

<400> SEQUENCE: 42
tcgtcgttta ggttatcgt                                                  19
```